US012564327B2

(12) United States Patent
Tearney et al.

(10) Patent No.: US 12,564,327 B2
(45) Date of Patent: Mar. 3, 2026

(54) METHODS AND SYSTEMS FOR CONVERSION OF ONE DATA TYPE TO ANOTHER

(71) Applicant: The General Hospital Corporation, Boston, MA (US)

(72) Inventors: Guillermo Tearney, Boston, MA (US); David O. Otuya, Salem, MA (US)

(73) Assignee: The General Hospital Corporation, Boston, MA (US)

( * ) Notice: Subject to any disclaimer, the term of this patent is extended or adjusted under 35 U.S.C. 154(b) by 147 days.

(21) Appl. No.: 18/562,940

(22) PCT Filed: May 23, 2022

(86) PCT No.: PCT/US2022/030526
§ 371 (c)(1),
(2) Date: Nov. 21, 2023

(87) PCT Pub. No.: WO2022/246314
PCT Pub. Date: Nov. 24, 2022

(65) Prior Publication Data
US 2024/0260834 A1 Aug. 8, 2024

Related U.S. Application Data

(60) Provisional application No. 63/191,397, filed on May 21, 2021.

(51) Int. Cl.
A61B 5/00 (2006.01)
G06T 5/50 (2006.01)
G06T 7/33 (2017.01)

(52) U.S. Cl.
CPC .......... A61B 5/0066 (2013.01); A61B 5/0084 (2013.01); G06T 5/50 (2013.01);
(Continued)

(58) Field of Classification Search
CPC .................................................. A61B 5/0066
See application file for complete search history.

(56) References Cited

U.S. PATENT DOCUMENTS 8,403,481 B2 3/2013 Izatt et al.
10,478,058 B2 11/2019 Cheng et al.
(Continued)

FOREIGN PATENT DOCUMENTS

JP 2018-173366 A 11/2018
WO 2012100816 A1 8/2012
WO 2020020920 A1 1/2020

OTHER PUBLICATIONS

Sherman, M. et al., Signal Attenuation Due to Cavity Leakage, Journal of the Acoustical Society of America, 1988, 84(6):2163-2169.
(Continued)

*Primary Examiner* — Joseph M Santos Rodriguez
(74) *Attorney, Agent, or Firm* — QUARLES & BRADY LLP

(57) ABSTRACT

A method for generating a B-mode image of a sample, including: obtaining a plurality of M-mode frames from the sample using a probe; combining the plurality of M-mode frames into a montage, the montage comprising a plurality of A-lines corresponding to the respective plurality of M-mode frames; comparing adjacent A-lines of the montage to identify at least one pair of correlated A-lines; and removing one of the at least one pair of correlated A-lines from the montage to generate a B-mode image.

25 Claims, 21 Drawing Sheets

(52) U.S. Cl.
    CPC ...... *G06T 7/33* (2017.01); *G06T 2207/10101*
            (2013.01); *G06T 2207/20216* (2013.01)

(56)                    References Cited

U.S. PATENT DOCUMENTS

| 2013/0338510 A1 | 12/2013 | Tearney et al. |
| 2015/0374343 A1 | 12/2015 | Shan et al. |
| 2018/0271476 A1 | 9/2018 | Strassner et al. |
| 2020/0054306 A1 | 2/2020 | Mehanian et al. |
| 2021/0052256 A1 | 2/2021 | Berger et al. |

OTHER PUBLICATIONS

Song, K. et al., Novel Jumbo Biopsy Forceps for Surveillance of Inflammatory Bowel Disease: A Comparative Retrospective Assessment, Gastroenterology Research and Practice, vol. 2011, Article ID 671659, 5 pages.
Ullah, H. et al., M-mode Swept Source Optical Coherence Tomography for Quantification of Salt Concentration in Blood: An In Vitro Study, Laser Physics, 2012, 22:1002-1010.
Valiantzas, J., Modified Hazen-Williams and Darcy-Weisbach Equations for Friction and Local Head Losses Along Irrigation Laterals, Journal of Irrigation and Drainage Engineering, 2005, 131(4):342-350.
Whiteside, S. et al., The Microbiome of the Urinary Tract—A Role Beyond Infection, Nature Reviews Urology, 2015, 12(2):81-90.
Woodard, H. et al. The Composition of Body Tissues, British Journal of Radiology, 1986, 59(708):1209-1218.
PCT International Search Report and Written Opinion, PCT/US2022/030526, Sep. 22, 2022, 9 pages.
Amornyotin, S. et al., Sedation-Related Complications in Gastrointestinal Endoscopy, World Journal of Gastrointestinal Endoscopy, 2013, 5(11):527-533.
Babiak, A. et al., Transbronchial Cryobiopsy: A New Tool for Lung Biopsies, Respiration, 2009, 78(2):203-208.
Bampton, P. et al., A Comparison of Transnasal and Transoral Oesophagogastroduodenoscopy, Journal of Gastroenterology and Hepatology, 1998, 13(6):579-584.
Barkun, A. et al., Update on Endoscopic Tissue Sampling Devices, Gastrointestinal Endoscopy, 2006, 63(6):741-745.
Bonacina, C. et al., Numerical Solution of Phase-Change Problems, International Journal of Heat and Mass Transfer, 1973, 16(10):1825-1832.
Chen, N. et al., New Generalized Equation for Gas Diffusion Coefficient, Journal of Chemical and Engineering Data, 1962, 7(1):37-41.
Corley, D. et al., Impact of Endoscopic Surveillance on Mortality from Barrett's Esophagus—Associated Esophageal Adenocarcinomas, Gastroenterology, 2013, 145(2):312-319.
Cummins, A. et al., Morphometric Evaluation of Duodenal Biopsies in Celiac Disease, Journal of the American College of Gastroenterology, 2011, 106(1):145-150.
Dieterich, W. et al., Microbiota in the Gastrointestinal Tract, Medical Sciences, 2018, 6(4):116, 15 pages.
Diller, K., Modeling of Bioheat Transfer Processes at High and Low Temperatures, Advances in Heat Transfer, 1992, 22:157-357.
Douglas, G. et al., Multi-omics Differentially Classify Disease State and Treatment Outcome in Pediatric Crohn's Disease, Microbiome, 2018, 6:1-12.
Egorov, V. et al., Mechanical Properties of the Human Gastrointestinal Tract, Journal of Biomechanics, 2002, 35 (10):1417-1425.
Fischer, H. et al., Average Protein Density is a Molecular-Weight-Dependent Function, Protein Science, 2004, 13 (10):2825-2828.
Franke, K. et al., A New Tool for Transbronchial Cryobiopsies in the Lung: An Experimental Feasibility ex vivo Study, Respiration, 2016, 91(3):228-234.
Friedel, D. et al., Gastrointestinal Endoscopy in the Pregnant Woman, World Journal of Gastrointestinal Endoscopy. 2014, 6(5):156-167.

Gibson, A. et al., A Simple and Improved Method to Determine Cell Viability in Burn-Injured Tissue, Journal of Surgical Research, 2017, 215:83-87.
Gonzalez, L. et al., Porcine Models of Digestive Disease: The Future of Large Animal Translational Research, Translational Research, 2015, 166(1):12-27.
Gorelick, A. et al., Unsedated Small-Caliber Esophagogastroduodenoscopy (EGD): Less Expensive and Less Time-Consuming than Conventional EGD, Journal of Clinical Gastroenterology, 2001, 33(3):210-214.
Goutal-Landry, C. et al., Effect of Endoscopic Forceps on Quality of Duodenal Mucosal Biopsy in Healthy Dogs, Journal of Veterinary Internal Medicine, 2013, 27(3):456-461.
Goyal, R. et al., Mechanical Properties of the Esophageal Wall, Journal of Clinical Investigation, 1971, 50 (7):1456-1465.
Gross, S. et al., Increased Detection of Barrett's Esophagus and Esophageal Dysplasia with Adjunctive Use of Wide-Area Transepithelial Sample with Three-Dimensional Computer-Assisted Analysis (WATS), United European Gastroenterology Journal, 2018, 6(4):529-535.
Harrison, R. et al., Detection of Intestinal Metaplasia in Barrett's Esophagus: An Observational Comparator Study Suggests the Need for a Minimum of Eight Biopsies, Official Journal of the American College of Gastroenterology, 2007, 102(6):1154-1161.
Havenith, G. et al., Evaporative Cooling: Effective Latent Heat of Evaporation in Relation to Evaporation Distance from the Skin, Journal of Applied Physiology, 2013, 114(6):778-785.
Helmers, R. et al., Overall Cost Comparison of Gastrointestinal Endoscopic Procedures with Endoscopist- or Anesthesia-Supported Sedation by Activity-Based Costing Techniques, Mayo Clinic Proceedings: Innovations, Quality & Outcomes, 2017, 1(3):234-241.
Huh, C. et al., Individual Variations in Mucosa and Total Wall Thickness in the Stomach and Rectum Assessed via Endoscopic Ultrasound, Physiological Measurement, 2003, 24(4):N15-N22.
Hulten, L. et al., Blood Flow in the Small Intestine of Cat and Man as Analyzed by an Inert Gas Washout Technique, Gastroenterology, 1976, 70(1):45-51.
Jones, F. et al., ITS-90 Density of Water Formulation for Volumetric Standards Calibration, Journal of Research of the National Institute of Standards and Technology, 1992, 97(3):335-340.
Lee, J. et al., Motion Correction for Phase-Resolved Dynamic Optical Coherence Tomography Imaging of Rodent Cerebral Cortex, Optics Express, 2011, 19(22):21258-21270.
Lentz, R. et al., Transbronchial Cryobiopsy for Diffuse Parenchymal Lung Disease: A State-of-the-Art Review of Procedural Techniques, Current Evidence, and Future Challenges, Journal of Thoracic Disease, 2017, 9(7):2186-2203.
Lervik, A. et al., Heat Transfer in Protein—Water Interfaces, Physical Chemistry Chemical Physics, 2010, 12 (7):1610-1617.
Liang, C. et al., Optical Coherence Tomography-Guided Laser Marking with Tethered Capsule Endomicroscopy in Unsedated Patients, Biomedical Optics Express, 2019, 10(3):1207-1222.
Lightdale, J. et al., Modifications in Endoscopic Practice for Pediatric Patients, Gastrointestinal Endoscopy, 2014, 79(5):699-710.
Lin, O., Sedation for Routine Gastrointestinal Endoscopic Procedures: A Review on Efficacy, Safety, Efficiency, Cost and Satisfaction, Intestinal Research, 2017, 15(4):456-466.
Litwin, K. et al., Influence of Temperature, Composition, and Grain Size on the Tensile Failure of Water Ice: Implications for Erosion on Titan, Journal of Geophysical Research, 2012, 117:E08013, 14 pages.
Lynch, S., The Lung Microbiome and Airway Disease, Annals of the American Thoracic Society, 2016, 13 (Supplement 5):S462-S465.
Malviya, S. et al., Prolonged Recovery and Delayed Side Effects of Sedation for Diagnostic Imaging Studies in Children, Pediatrics, 2000, 105(3):e42, 5 pages.
Matsuo, Y. et al., Endoscopic Small-Capacity Forceps Increase the Pathological Diagnosis of Gastric Indefinite Neoplasia, Turkish Journal of Gastroenterology, 2018, 29(4):481-487.
Melinder, A., Thermophysical Properties of Aqueous Solutions Used as Secondary Working Fluids, PhD. Doctoral Thesis, Royal Institute of Technology, KTH, 2007, 144 pages.

(56)             References Cited

OTHER PUBLICATIONS

Mohammadi, E. et al., A Study of the Phase Change in Three Phase Environment, 21st Australasian Fluid Mechanics Conference, 2018, 4 pages.

Moinuddin, Z. et al., Encapsulating Peritoneal Sclerosis—A Rare but Devastating Peritoneal Disease, Frontiers in Physiology, 2015, vol. 5, Article 470, pp. 1-11.

Narasimhan, T. et al., Fourier's Heat Conduction Equation: History, Influence, and Connections, Reviews of Geophysics, 1999, 37(1):151-172.

Parker, C. et al., Transnasal Endoscopy: No Gagging No. Panic!, Frontline Gastroenterology, 2016, 7(4):246-256.

Peery, A. et al., Burden and Cost of Gastrointestinal, Liver, and Pancreatic Diseases in the United States: Update 2018, Gastroenterology, 2019, 156(1):254-272.

Peterson, D. et al., Metagenomic Approaches for Defining the Pathogenesis of Inflammatory Bowel Diseases, Cell Host & Microbe, 2008, 3(6):417-427.

Prabhku, N. et al., Heat Capacity in Proteins, Annu. Rev. Phys. Chem., 2005, 56:521-548.

Ramires, M. et al., Standard Reference Data for the Thermal Conductivity of Water, Journal of Physical and Chemical Reference Data, 1995, 24(3):1377-1381.

Rodriguez, S. et al., Ultrathin Endoscopes, Gastrointestinal Endoscopy, 2010, 71(6):893-898.

Said, M. et al., Analytical and Numerical Calculation of the Orifice Minimum Temperature Due to Joule-Thomson Effect, Fluid Mechanics, 2017, 3(5):42-52.

Schlottke, J. et al., Direct Numerical Simulation of Evaporating Droplets, Journal of Computational Physics, 2008, 227(10):5215-5237.

Notification of Reasons for Refusal in Japanese Application No. 2023-571951; received on Sep. 2, 2025.

METHODS AND SYSTEMS FOR CONVERSION OF ONE DATA TYPE TO ANOTHER

CROSS-REFERENCE TO RELATED APPLICATIONS

The present application represents the U.S. national stage entry of international Patent Application Ser. No. PCT/US2022/030526, filed on May 23, 2022, which is based on and claims priority from U.S. Patent Application Ser. No. 63/191,397, filed on May 21, 2021, the entire disclosures of which are incorporated herein by reference.

STATEMENT REGARDING FEDERALLY SPONSORED RESEARCH

N/A

BACKGROUND

Optical coherence tomography (OCT) is a non-contact imaging modality that uses low-coherence light to provide high-resolution, high-speed, cross-sectional tomographic imaging of body internal structures and materials. OCT can be used for imaging tissue in vivo in the body or ex vivo on the benchtop. Tissue imaging ex vivo generally involves scanning an optical beam using a galvanometer scanner over the area of interest on the tissue. In vivo OCT imaging, on the other hand, can take two forms: the mechanical scanner for beam scanning can be located inside the optical catheter in the body, an architecture known as distal scanning, or the mechanical scanner can be located outside the body, an architecture known as proximal scanning. The advantage of proximal scanning is the ability of to use small diameter optical probes (>300 μm), making it possible to image small luminal organs such as arteries. The main drawback to this method of OCT imaging is the huge cost and effort required to develop the proximal scanning module known as an optical rotary junction (RJ). Furthermore, ex vivo OCT imaging requires an elaborate costly setup of a galvanometer scanner which is bulky and costly.

SUMMARY OF THE INVENTION

Accordingly, new systems, methods, and media for generating B-mode images from a sample using OCT imaging are desirable.

Disclosed herein are methods, systems, and apparatus that can be used to perform both in vivo and ex vivo tissue imaging using an interferometric modality such as OCT that obviates the need for an elaborate scanning setup. In various embodiments, the disclosed methods, systems, and apparatus may be used to perform manual scanning of an optical probe over a tissue surface of interest without any requirement for a separate device for mechanical scanning. Removing the requirement for mechanical scanning of the probe means that smaller probes can be used (e.g., when there is not a need for the probe to include a torque coil, the resulting probe without a torque coil can have a diameter as small as 80 μm), lower-cost probes can be used, and smaller spaces (e.g., orifices) can be imaged using the probe.

One embodiment provides a method for generating a B-mode image of a sample, including: obtaining a plurality of M-mode frames from the sample using a probe; combining the plurality of M-mode frames into a montage, the montage comprising a plurality of A-lines corresponding to the respective plurality of M-mode frames; comparing adjacent A-lines of the montage to identify at least one pair of correlated A-lines; and removing one of the at least one pair of correlated A-lines from the montage to generate a B-mode image.

Another embodiment provides a system for generating a B-mode image of a sample, including: an optical probe coupled to an electromagnetic radiation source and a detector; and a processor coupled to the electromagnetic radiation source and the detector and configured to: obtain a plurality of M-mode frames from the sample; combine the plurality of M-mode frames into a montage, the montage comprising a plurality of A-lines corresponding to the respective plurality of M-mode frames; compare adjacent A-lines of the montage to identify at least one pair of correlated A-lines; and remove one of the at least one pair of correlated A-lines from the montage to generate a B-mode image.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with some embodiments of the disclosed subject matter, mechanisms (which can include methods, systems, and apparatus) for collecting and processing interferometric data and generating B-mode images are provided. Although in many cases the exemplary embodiments disclosed herein are presented in the context of converting M-mode data to B-mode images, the mechanisms disclosed herein are more generally applicable for converting one data type to another.

Figure 1:
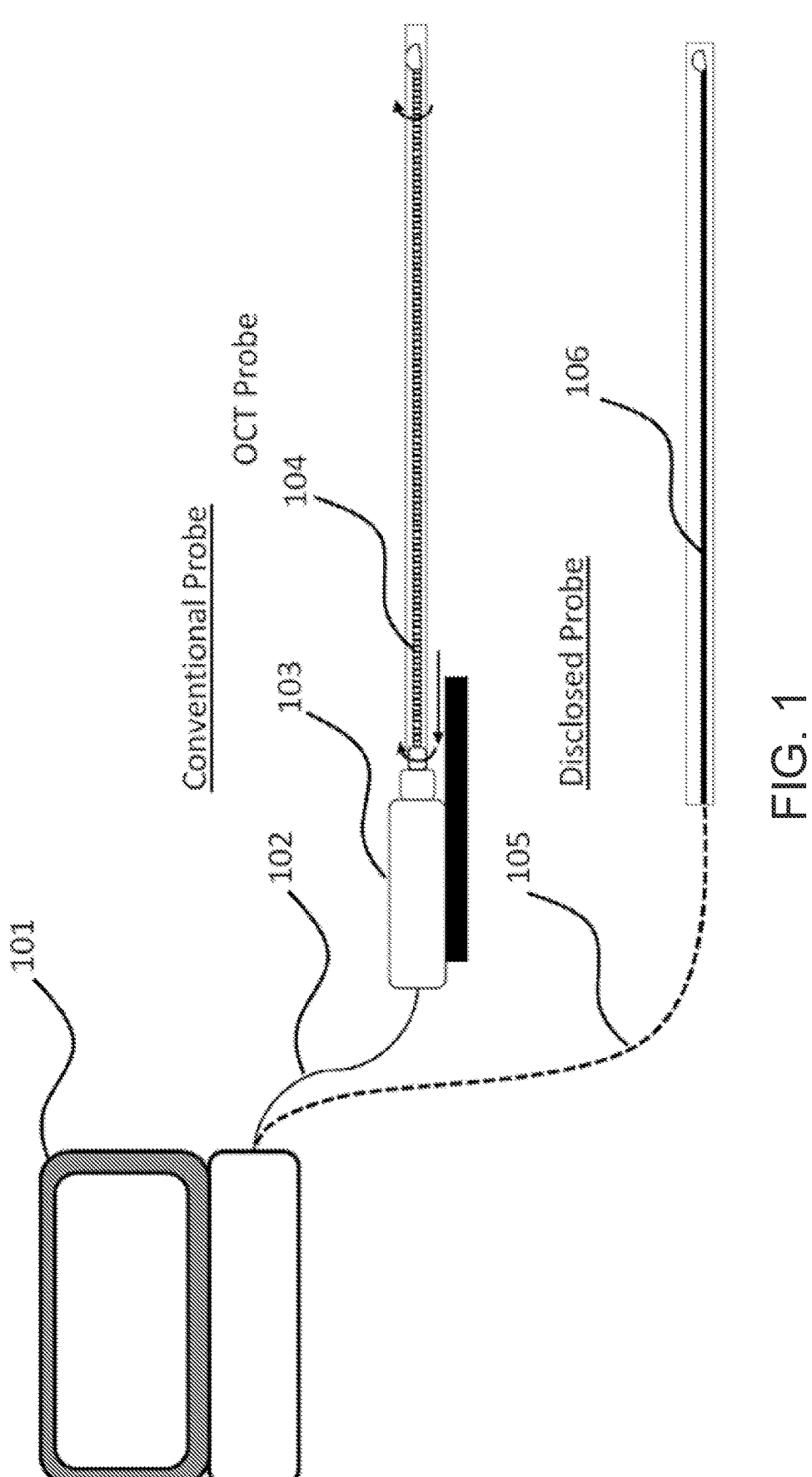
FIG. 1 shows an OCT imaging system coupled to either a conventional probe having a torque coil, a rotary junction, and a pull-back mechanism (top) or a probe according to certain embodiments which does not include a torque coil, rotary junction, or pull-back mechanism.

FIG. 1 shows an OCT imaging system 101 coupled by a waveguide 102 to a conventional probe having a torque coil 104 and a rotary junction with a pull-back mechanism 103 (top). FIG. 1 also shows the OCT imaging system 101 coupled via a waveguide 105 to a probe 106 according to certain disclosed embodiments which does not include a torque coil, rotary junction, or pull-back mechanism and instead includes a single monolithic probe.

Figure 2:
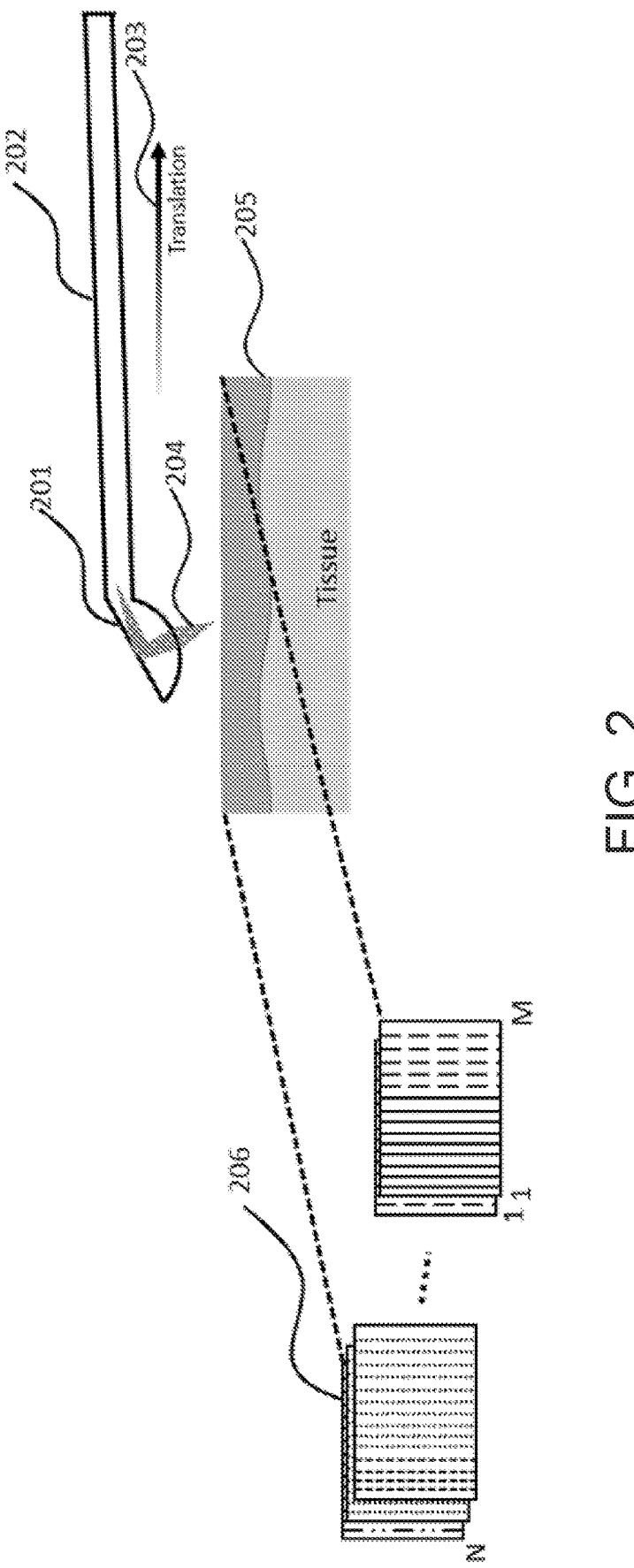
FIG. 2 provides an overview of data collection, showing how the probe moves along an elongated sample and collects a series of M-mode tomogram frames corresponding to different points along the sample.

FIG. 2 provides an overview of data collection, showing how the probe 202 moves along an elongated sample 205 and collects a series of M-mode tomogram frames corresponding to different points along the sample. In general, each of the M-mode frames includes a linear array of data which corresponds to data collected at varying depths within the sample 205. FIG. 2 shows a distal end ('distal' referring to the end of the probe which is closest to the sample and furthest from the operator) of an optical probe 202 with a polished ball lens 201, where the polished surface acts as a reflector to reflect light 204 from the waveguide into the sample 205 and to reflect light reflected from the sample back into the waveguide. When the optical probe 202 is manually pulled along the tissue surface (e.g., in a direction indicated by arrow 203), several OCT image frames 206 (M-mode frames or tomograms) are acquired which correspond to points along the tissue 205. Each OCT M-mode frame 206 may contain information relating to a single location on the tissue surface or may contain information from several locations along the tissue surface.

Given that the frames 206 are collected at regular time intervals while using a manual pullback, the physical spacing between successive frames may be variable. For example, the manually-scanned probe may move slower or faster at different points in time, with a result that some frames may cover overlapping portions of the sample (e.g., from data collected during periods of slower scanning) or may cover more evenly- or widely-spaced portions of the sample (e.g., from data collected during periods of faster scanning). Therefore, procedures are needed to analyze the data and, if necessary, to identify and remove duplicate frames that arise from periods of slower scanning.

Figure 3:
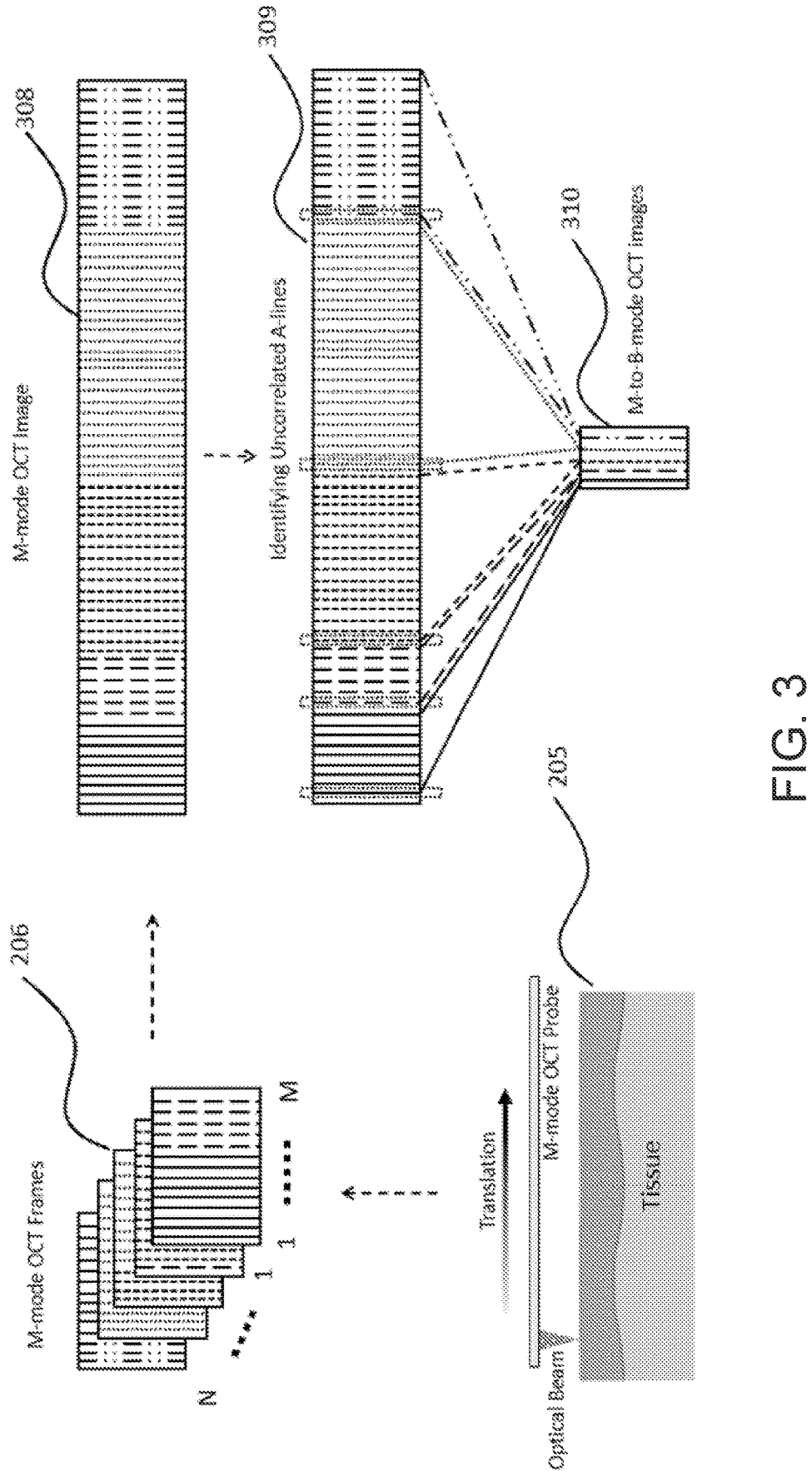
FIG. 3 provides an overview of a process for converting a series of M-mode tomogram frames into a single B-mode image.

FIG. 3 provides an overview of a process for converting a series of M-mode tomogram frames 307 into a single B-mode image 310 (e.g., an OCT image), including a process for identifying and removing duplicate frames. Initially, a given number of M-mode frames 307 that have been collected may be combined or 'stitched' together into one long frame or montage 308, such that each M-mode frame corresponds to a column (or A-line) in the montage 308. The adjacent columns (A-lines) in the montage 308 may be compared to one another to determine a degree of similarity using a metric such as Pearson's cross correlation coefficient between the two lines to identify adjacent columns (corresponding to adjacent M-mode frames) that are similar or identical, which is taken as an indication that such frames were collected during a period of slower scanning. If the similarity metric (e.g., the cross-correlation coefficient) between the adjacent columns is above a set threshold, one of the two adjacent columns may be dropped off and the iteration through columns in the montage continued. As shown in FIG. 3, during processing of the montage 309, the redundant columns (shown as dashed vertical lines) may be eliminated and the non-redundant columns (shown as solid vertical lines) may be retained. The new restitched image 310 (which is made of the non-redundant columns that were not eliminated) is the B-mode image generated from the M-mode frames. In some embodiments, one or more of the similar or redundant A-lines may be averaged with one another into a single representative A-line in the final image.

Figure 4:
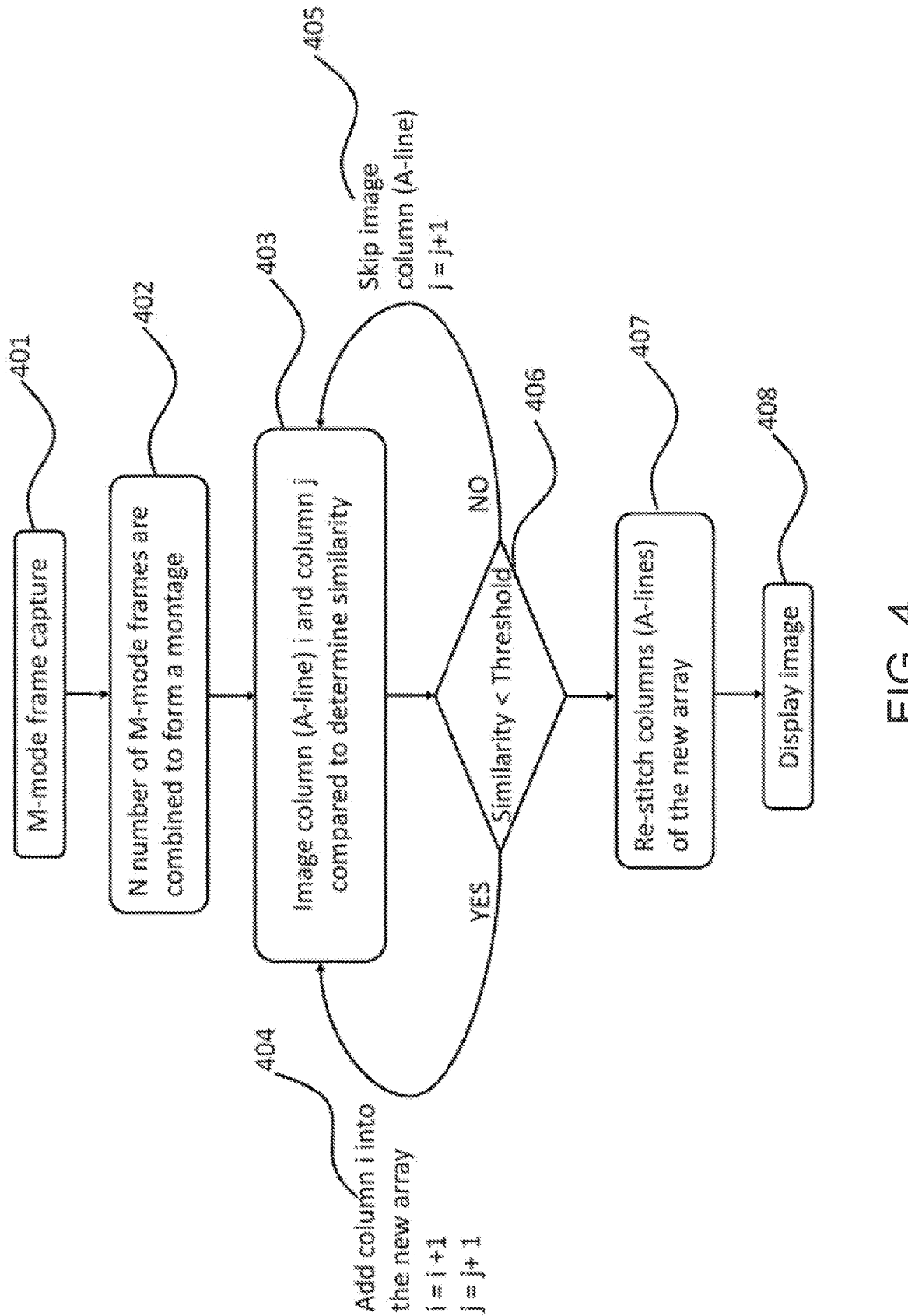
FIG. 4 provides a flow chart with steps for converting a series of M-mode frames or tomograms to a B-mode frame or image.

FIG. 4 provides a flow chart with steps for converting a series of M-mode frames or tomograms to a B-mode frame or image. At step 401, a number of M-mode frames are captured, for example using the procedures disclosed herein including using a manual pull-back mechanism. While the procedures disclosed herein are presented in the context of optical data obtained using a manual pull-back mechanism, the procedures could also be used on other types of data including optical data that is obtained using other pull-back procedures such as a mechanical (e.g. motor-driven) pull-back mechanism since the probe may at times advance in an uneven manner and thus may require the data to be compensated as disclosed herein.

At step 402, a given number (N) of M-mode frames may be combined to form a montage (M-mode OCT image), where the adjacent frames form a continuous image frame with the individual pixel columns known as A-lines. At step 403, two adjacent A-lines i and j may be compared to determine a degree of similarity or correlation, for example using a cross correlation analysis such as by computing Pearson's correlation coefficient r or using a similar method. At step 406, if the degree of similarity or correlation (e.g., as determined by calculating a cross correlation coefficient between the two columns) is less than a particular threshold, the column indexes i and j may be each increased by 1 at step 404 so that the next pair of adjacent A-lines are analyzed for similarity. On the other hand, if the cross-correlation coefficient is greater than or equal to the particular threshold, at step 405 one of the columns (e.g., image column j) may be removed and the new j index points to the j+1 column. After iterating through all the columns of the montage image, a new image is reconstituted at step 407 to form the new B-mode image. At step 408, this image may be stored, transmitted to another location or user, and/or displayed.

Figure 5:
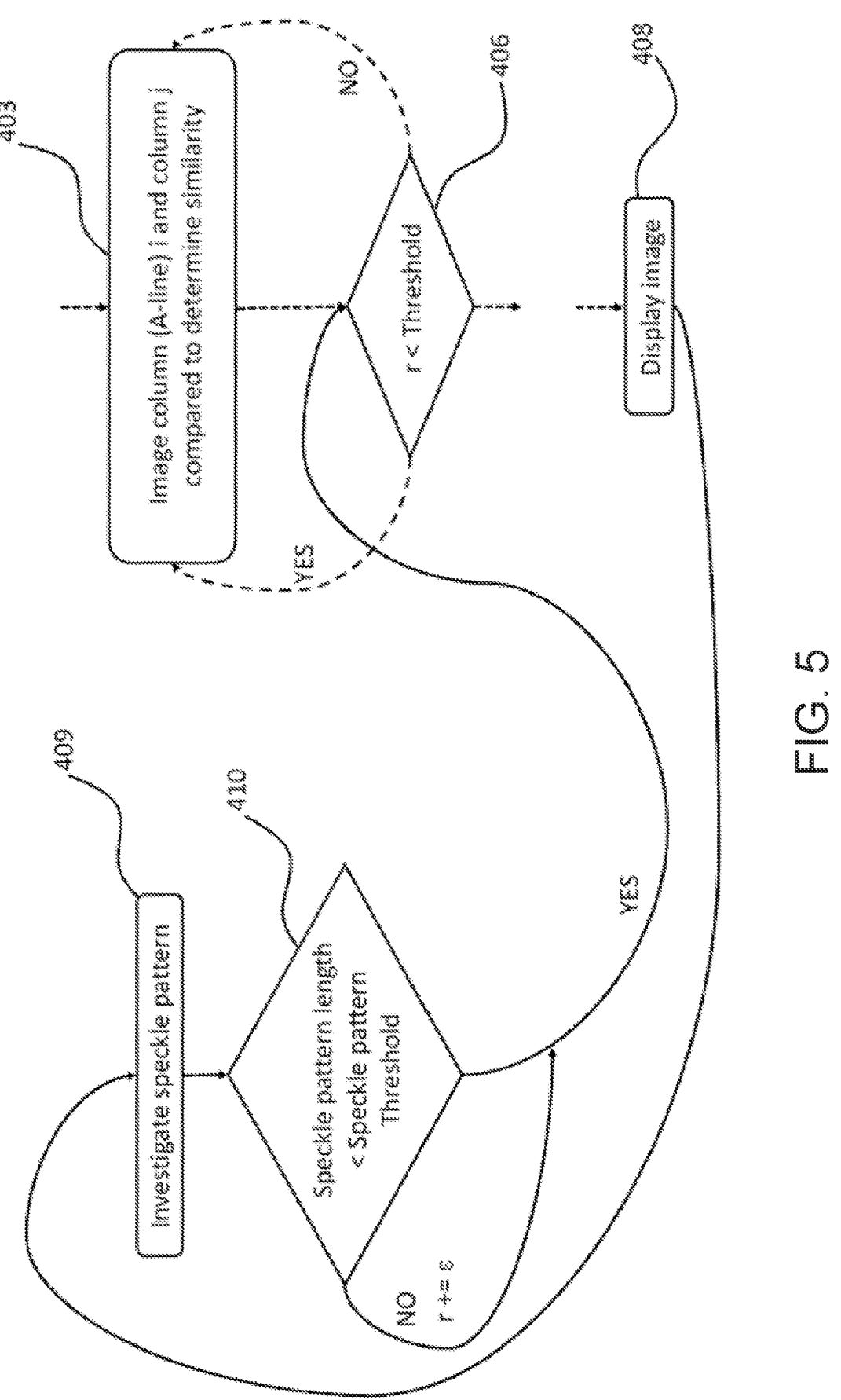
FIG. 5 provides an additional flow chart showing optional step(s) in the procedure of FIG. 4.

In various embodiments, additional step(s) may be included after step 408 to adjust the threshold used for comparing the adjacent image columns (FIG. 5). In some embodiments, the speckle pattern may be inspected or evaluated after the image is formed and if the speckle pattern length is greater than a fixed speckle pattern threshold, the cross-correlation threshold may be adjusted by a small fixed value F. The speckle size may be analyzed by processes such as space-frequency transform across the entire image, for example using a Wigner or short-time Fourier transform or a similar process. The adjusted threshold value may then be used to evaluate the degree of similarity at step 406.

In some embodiments, a procedure may be used to identify a particular manual scanning speed to use when collecting data, based on parameters of the particular optical system that is being employed to collect the data. The generated B-scan image can be examined to determine whether there exists an artifact in the image (e.g., evident discontinuities in the image); if so, the scanning speed can be decreased. As the scanning is performed at slower speeds, there tends to be more redundant M-mode frames in the collected data, which can be identified and removed using the procedures disclosed herein. On the other hand, if scanning is performed at speeds that are too fast, certain portions of the sample may be missed and not represented in the final B-scan image that is produced (which may be seen as evident discontinuities in the B-scan image); however, this missing data cannot be restored or recovered through post-processing and instead the sample must be re-scanned at a slower rate. The maximum imaging speed or scanning rate can be computed as $$v = \frac{f_s \Delta x}{\zeta},$$

where $f_s$ is the OCT imaging system A-line rate, $\Delta x$ is the optical beam spot size, and $\zeta$ is the oversampling rate which is usually 2.

The A-line rate indicates how quickly the system obtains a single M-mode frame A-line (i.e., how quickly a depth scan at a single location can be performed); $\Delta x$ indicates the area covered by each A-line; and the oversampling rate indicates the rate at which data is collected (generally at twice the spatial resolution) to avoid artifacts such as aliasing. Therefore, the equation above takes into account how quickly data from a spatial unit of the sample can be collected using the particular imaging probe and system and divides by the oversampling rate to determine the maximum imaging speed.

Figure 6A:
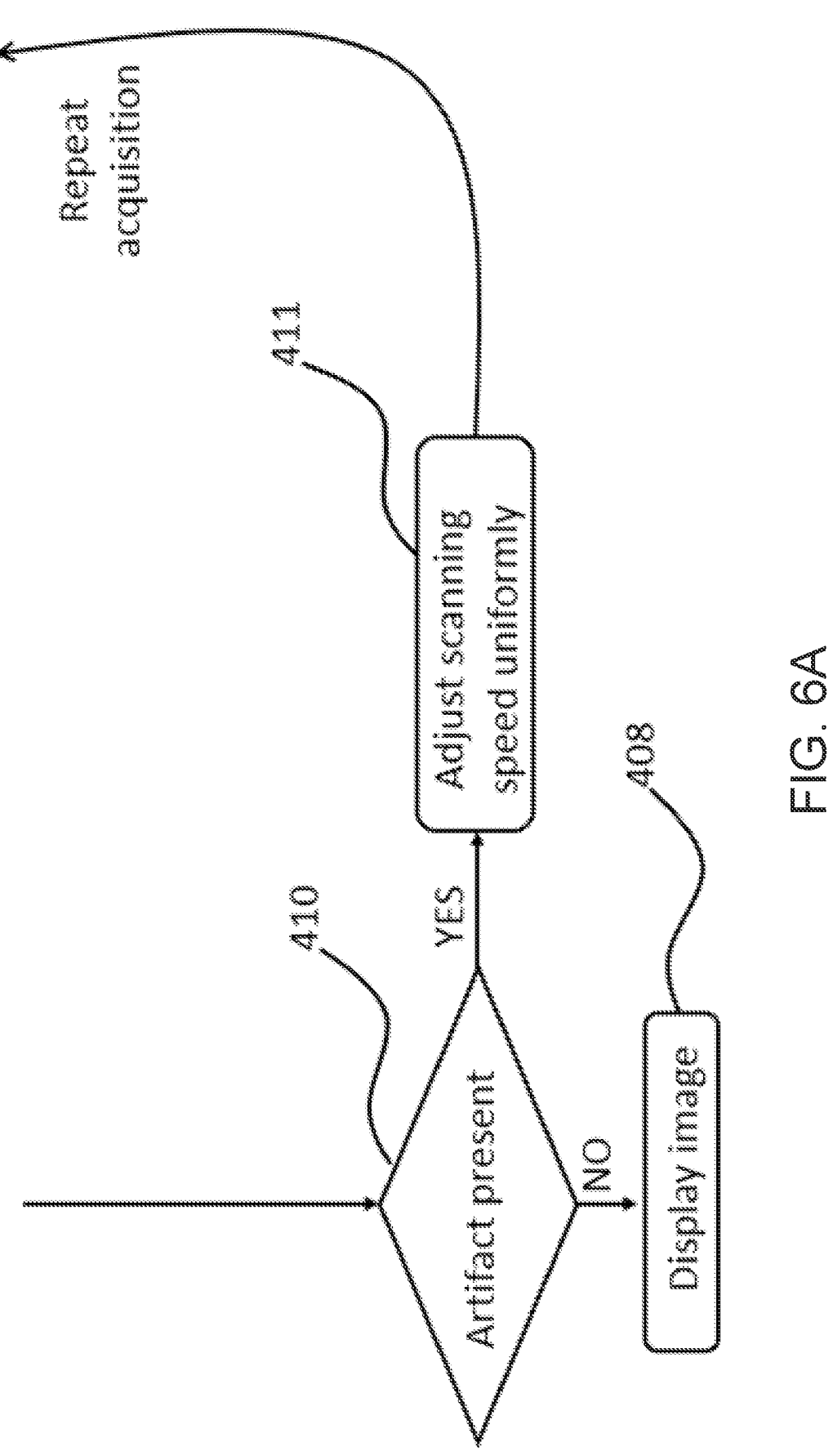
FIG. 6A provides an additional flow chart showing optional step(s) in the procedure of FIG. 4.

FIG. 6A shows an embodiment of the procedure in which additional step(s) may be added prior to the final step 408 (labeled as "Display image"). These step(s) may include determining whether an artifact is present 410 and, if so, uniformly adjusting the scanning speed 411 (e.g., based on the maximum imaging speed for the system determined as outlined above) and repeating acquisition. Re-scanned images can then be evaluated for evidence of artifacts and, if none are apparent, the image may be stored, transmitted to another location or user, and/or displayed at step 408.

Figure 6B:
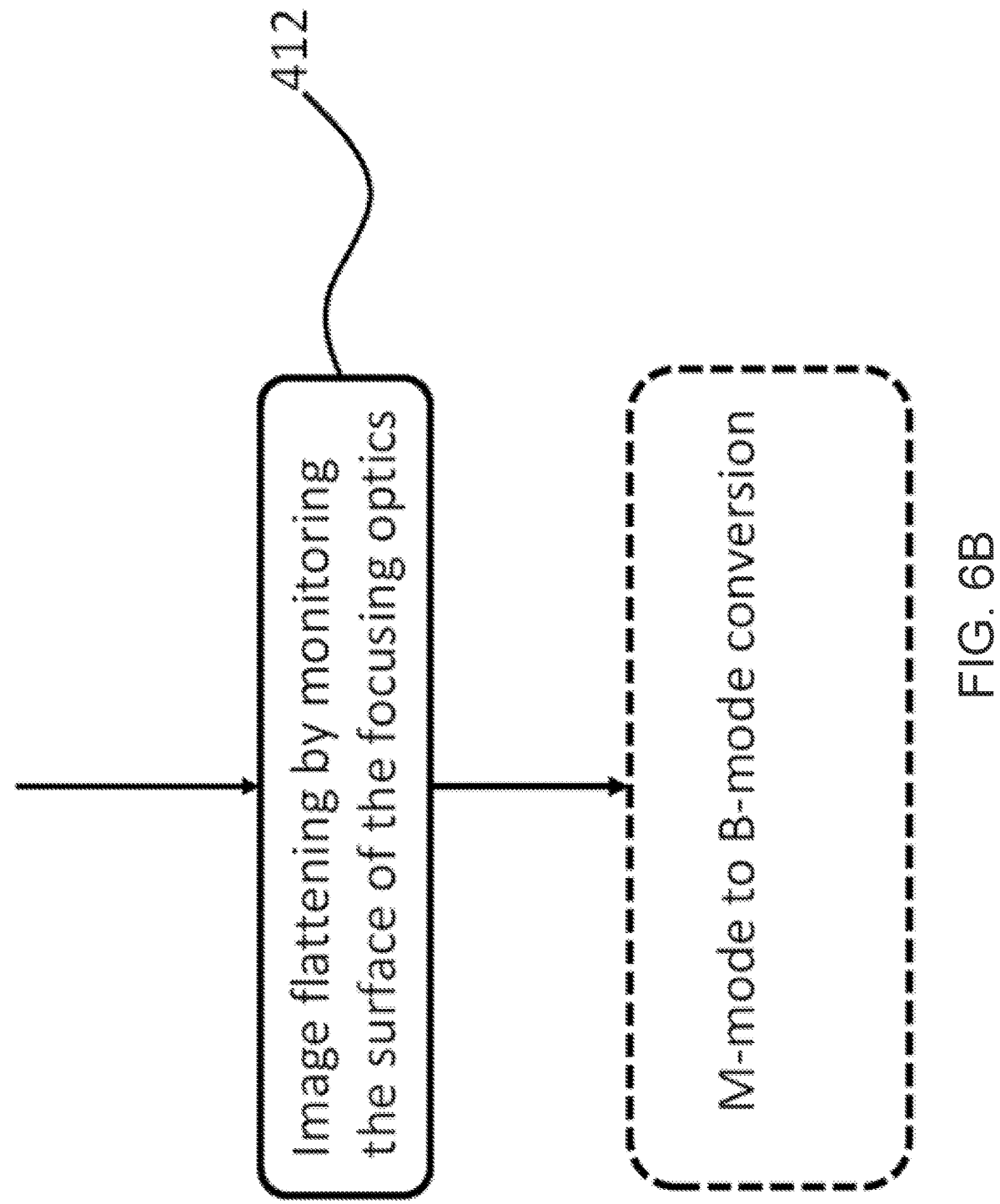
FIG. 6B shows a flow chart including a step for improving depth performance.

In some embodiments, depth performance of the M-mode to B-mode image conversion algorithm can be improved by monitoring the image surface (see FIG. 6B). The image surface can be monitored by probing the reflection from the focusing optics and using that information to flatten the image. For example, this can be done by compensating for the curvature in the image by aligning all the bright spots corresponding to the reflection such that they are in a straight line. This procedure (step 412) can be performed prior to the M-mode to B-mode conversion, e.g., prior to step 403 (see FIG. 6B).

Figure 6C:
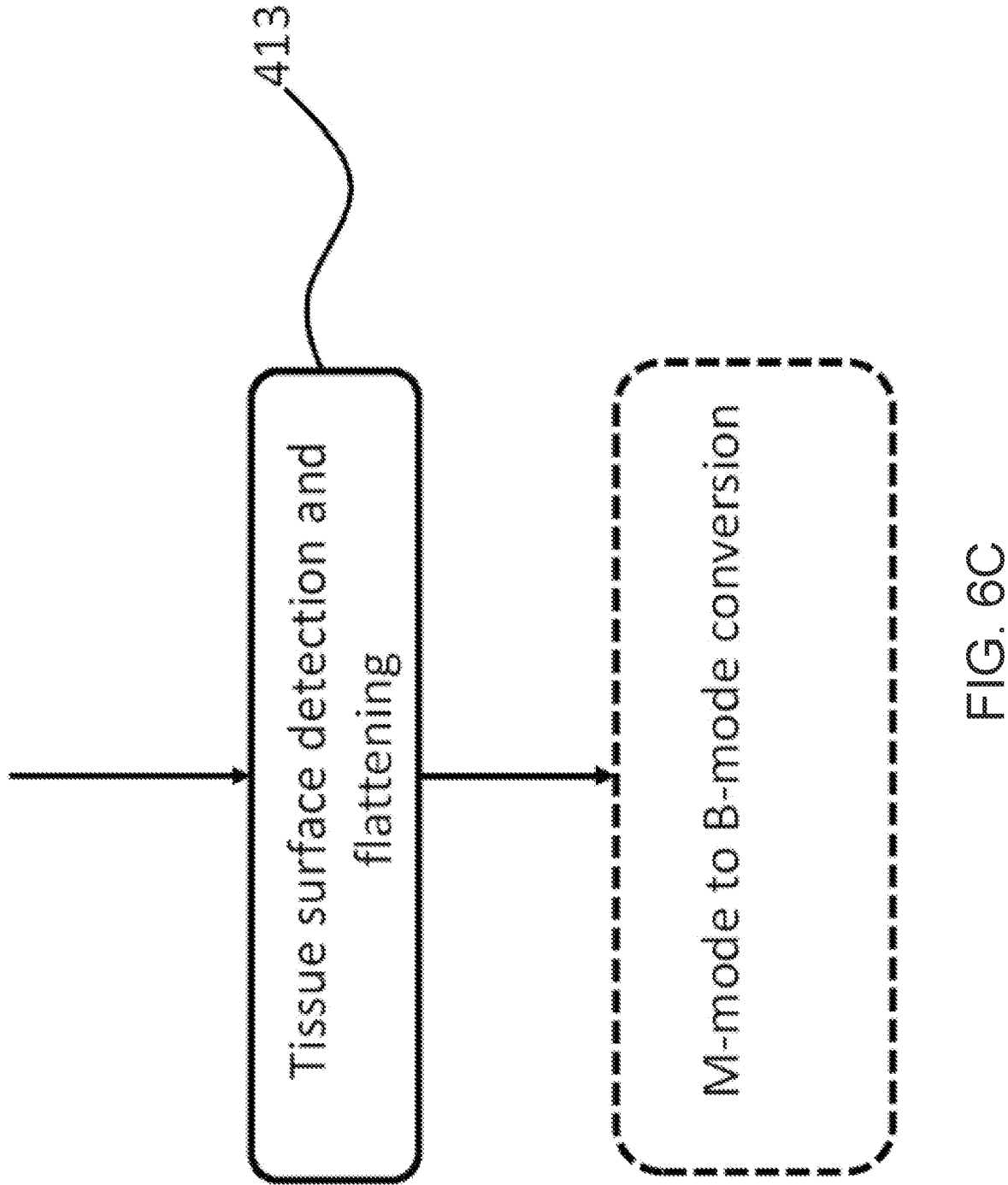
FIG. 6C shows a flow chart including a step for improving image quality by correcting for tissue surface curvature.

In other embodiments, the performance of the algorithm may be improved by correcting for tissue surface curvature (FIG. 6C). This procedure (step 413), which can be performed prior to the M-mode to B-mode conversion, e.g., prior to step 403, is done to ensure that the cross-correlation of the adjacent A-lines compares mainly the speckle pattern in the two A-lines instead of changes in the tissue surface.

Figure 7:
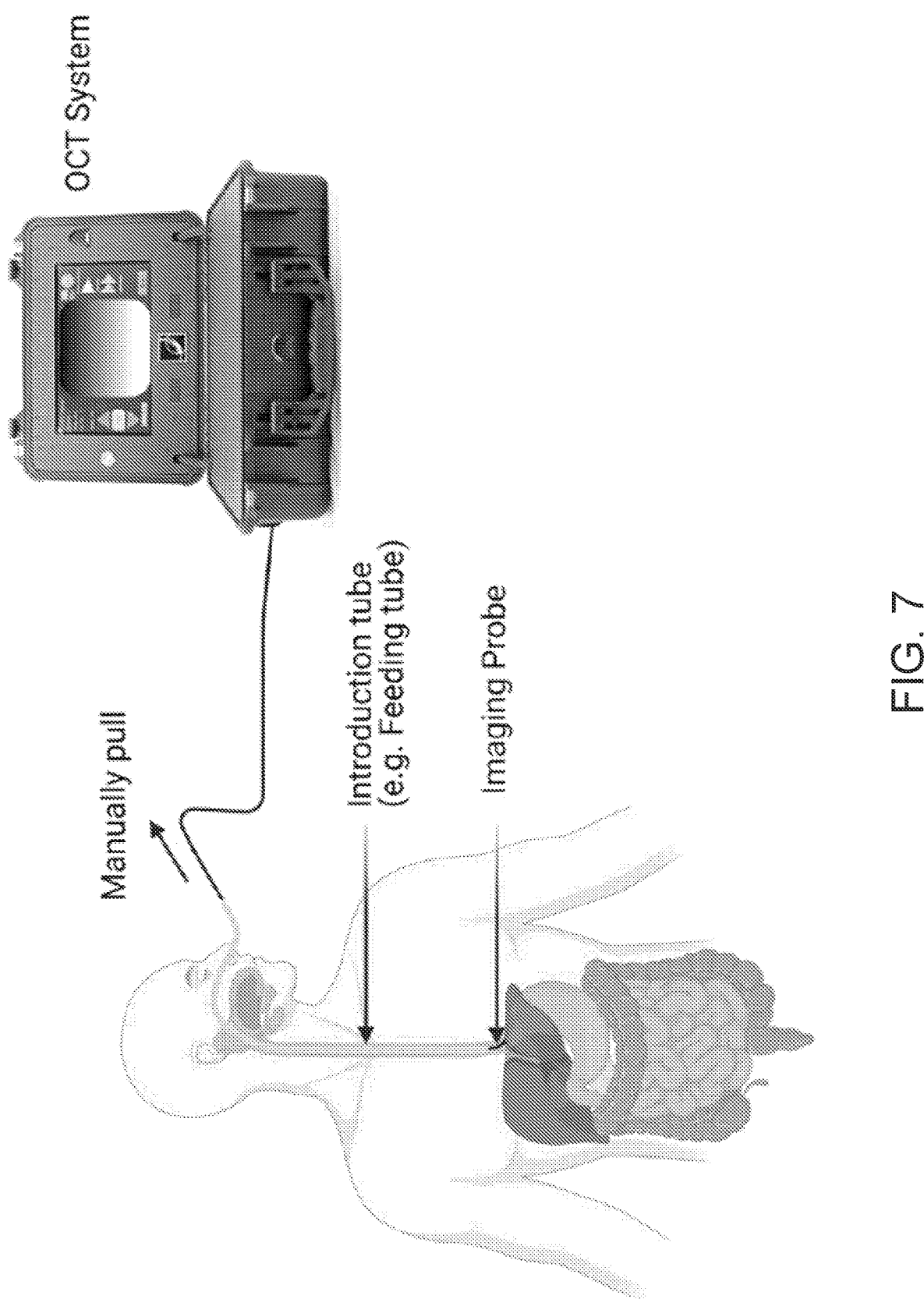
FIG. 7 provides a diagram of an OCT system being used to collect data from a luminal sample in a subject using the procedures disclosed herein including the disclosed probe.

FIG. 7 provides a diagram of an OCT system being used to collect data from a luminal sample in a subject (the esophagus of a human) using the procedures disclosed herein including the disclosed probe. An introduction tube is inserted along with the proposed optical probe into the GI tract of the subject via the nose/nasal cavity or a similar luminal organ. The optical probe is then pulled gently (e.g., at a rate of <1.25 m/s) while M-mode images are acquired; data collected using this procedure is then processed using the procedures disclosed herein.

Figure 8:
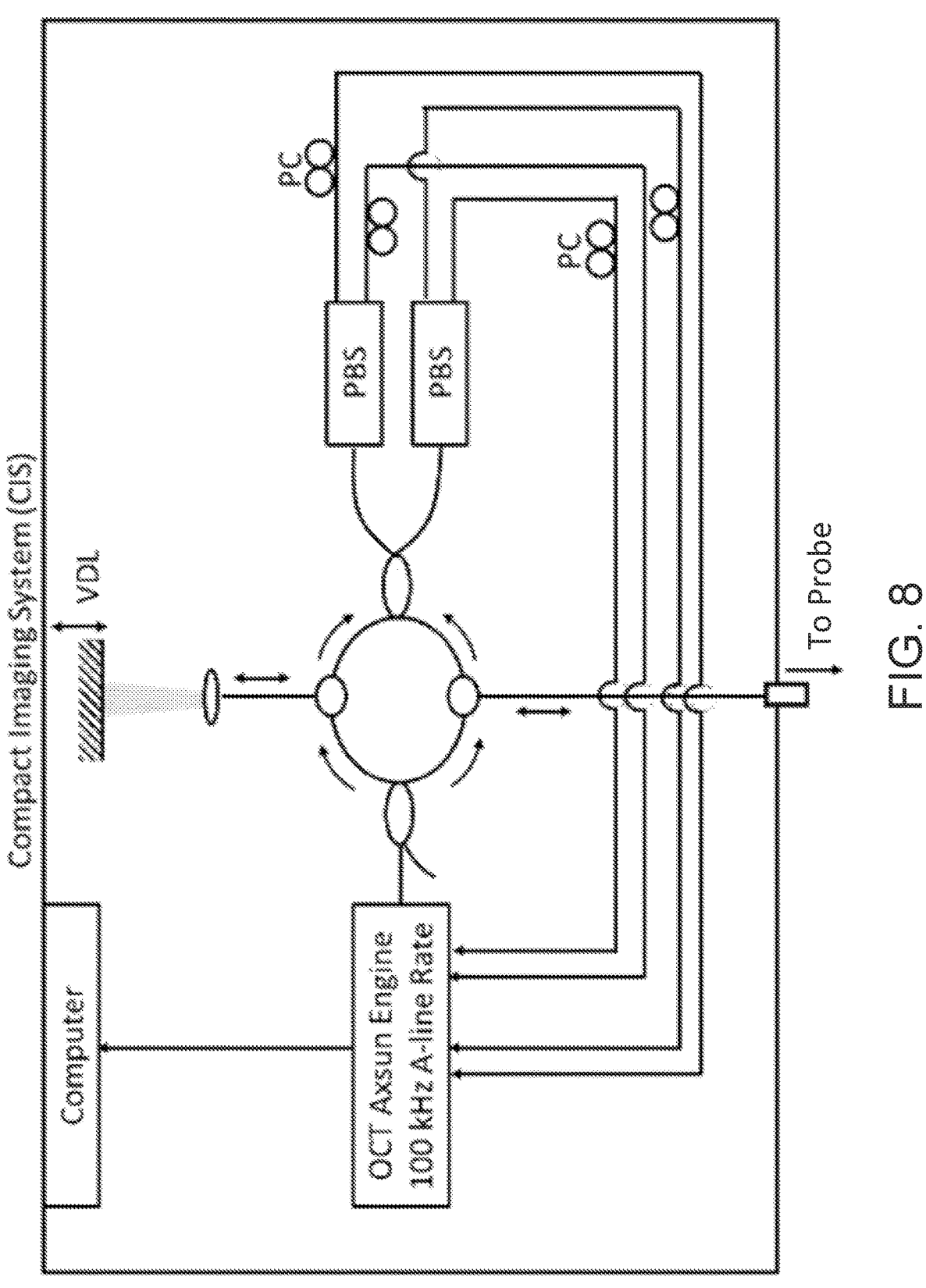
FIG. 8 shows a diagram of a system for contact sensing and high-resolution optical coherence tomography (OCT) imaging of tissue according to certain aspects of the disclosure including an OCT compact imaging system (CIS) including an Axsun engine (Axsun Technologies) running at 100 kHz; an interferometer consisting of one input beam splitter, two circulators, a reference arm with a variable delay line (VDL), a sample arm with connection to the Probe, an output coupler connected to a set of two polarization beam splitters (PBS); polarization controllers (PC) on the outputs from the PBS back to the Axsun engine; and a computer for processing and displaying the OCT signal.

FIG. 8 shows an embodiment of a data collection system that can be used to obtain data that can be processed using the procedures disclosed herein. This system includes a 10 μm-resolution, cross-sectional 100 kHz OCT Axsun engine (Axsun Technologies) with a light source of center wavelength 1310 nm, and bandwidth 140 nm. The output from the light source may be split into reference and sample beams having 20% and 80% of the light, respectively. The reference arm may be directed via an optical circulator to a mirror mounted on motorized stage (variable delay line (VDL)) and the sample arm may be connected to the optical probe via another circulator. The back-reflected light from both the reference and sample arms may be combined using an optical coupler to create an interference fringe pattern. The fringe pattern was collected using a polarization diverse system including two sets of polarization beam splitters (PBS), and four balanced diodes in the Axsun engine. OCT images may be generated and displayed using a computer coupled with the system. FIG. 7 shows the outward 8 appearance of such a system.

The optical probe may obtain M-mode images of the tissue to be biopsied. The OCT system may include an Axsun OCT engine (Axsun Technologies Inc.) with an A-line rate of 100 kHz. M-mode images captured by the probe may be combined into a montage and adjacent A-lines may be compared by computing their cross-correlation coefficients. Identical A-lines may be excluded by retaining A-lines whose cross-correlation coefficients are below a set threshold, as disclosed herein.

Figure 9:
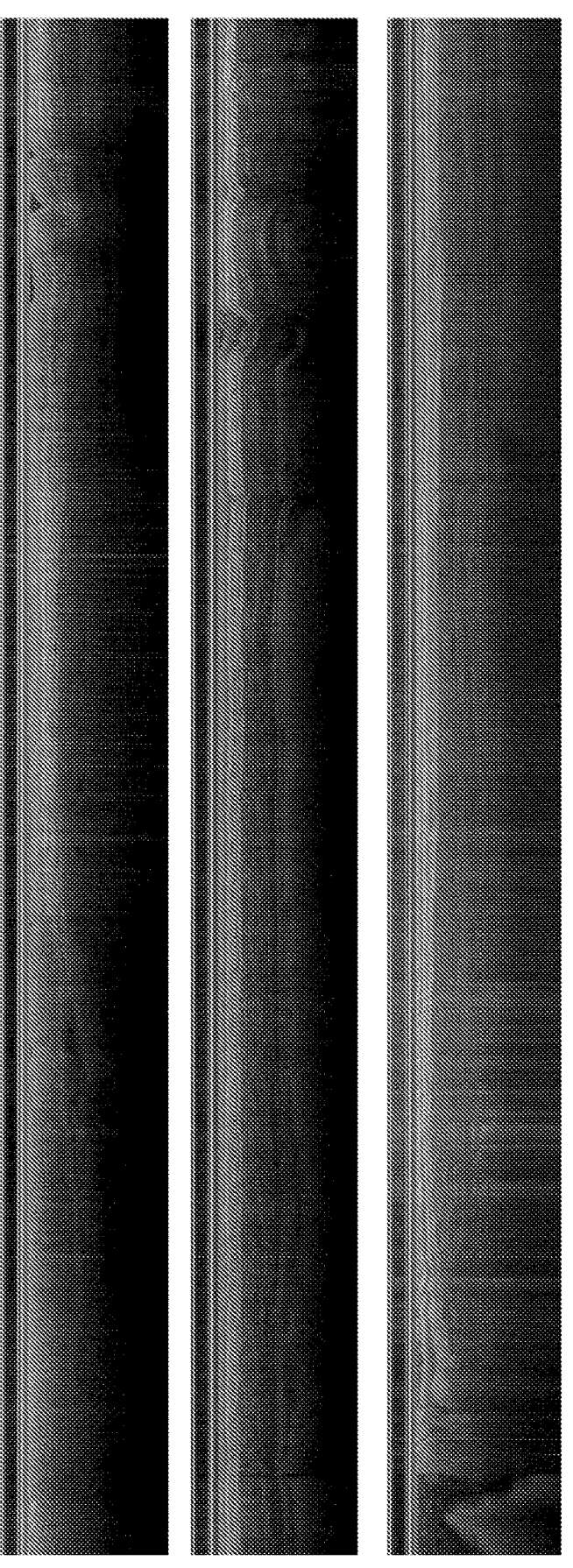
FIG. 9 and FIG. 10 provide B-mode images based on data collected from the esophagus and processed using the procedures disclosed herein.
Figure 10:
Figure 11:
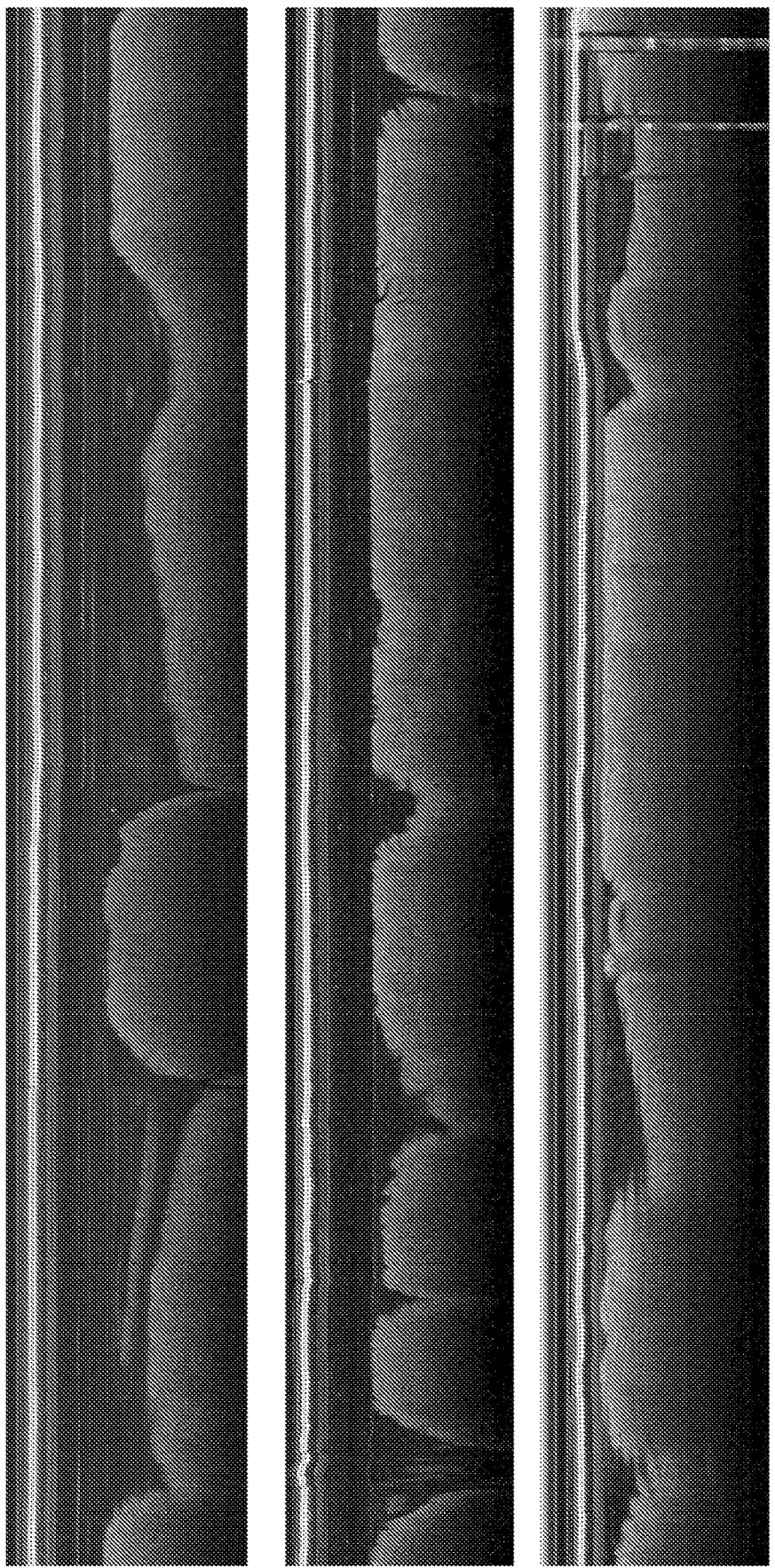
FIG. 11 provides B-mode images based on data collected from the duodenum and processed using the procedures disclosed herein.

FIG. 9 and FIG. 10 provide B-mode images based on data collected from the esophagus and processed using the procedures disclosed herein. FIG. 11 provides B-mode images based on data collected from the duodenum and processed using the procedures disclosed herein.

Figure 12:
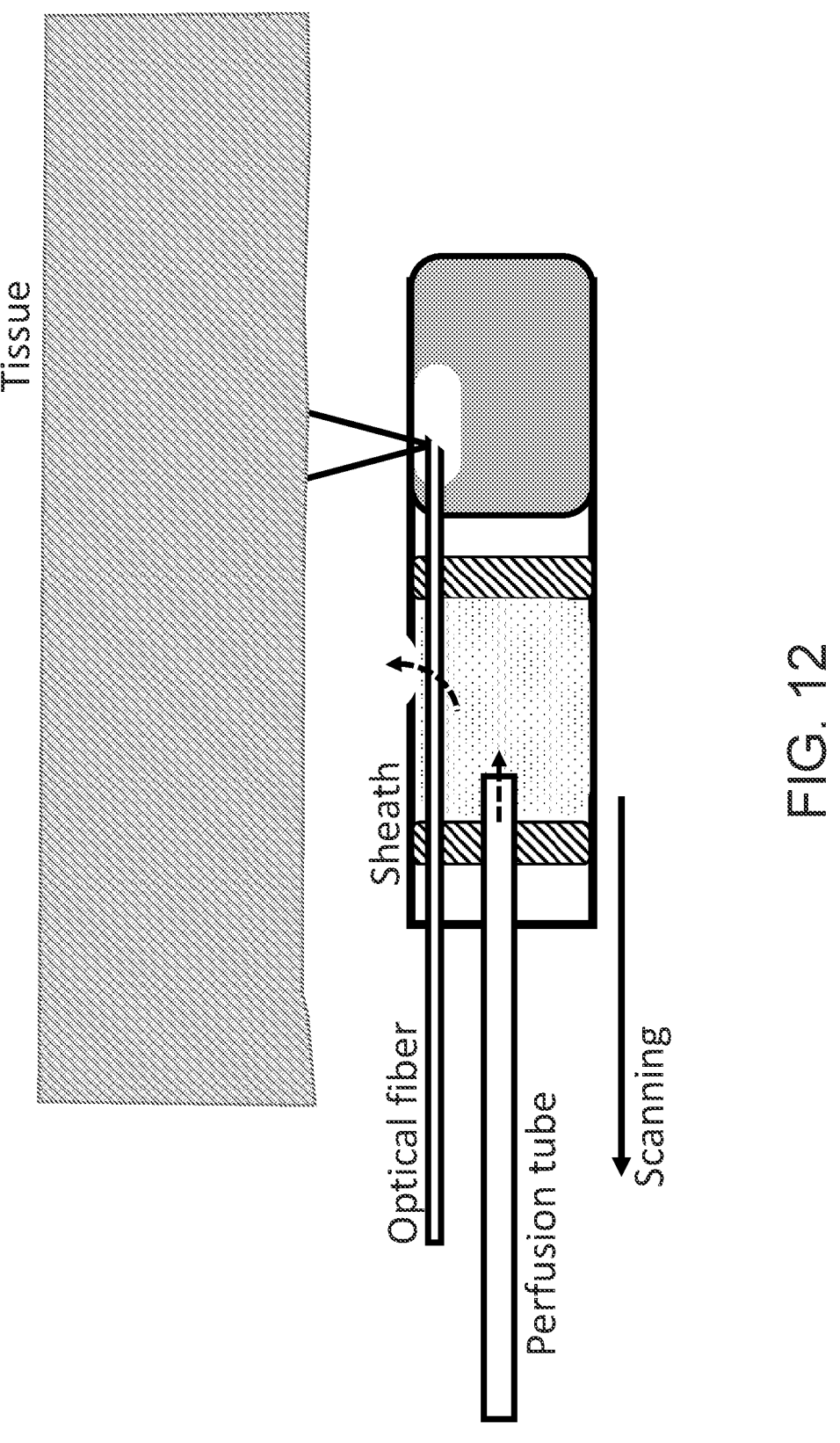
FIG. 12 shows an imaging probe according to some embodiments in which the fiber is offset from the center of the probe and an end of the optical fiber is polished.

In some embodiments, the optical probe that is used to collect data may be optimized for use in non-rotational data collection. Given that the probe may not be rotated and instead may be scanned across a sample in a single axial orientation, in certain embodiments the optical fiber may be disposed within the probe in an offset position closer to a side of the probe so that the end of the fiber is closer to the sample as well as being closer to the side of the probe from which electromagnetic radiation is emitted from the probe (see FIG. 12). In addition, with the fiber end being closer to the outer perimeter of the probe there is less material inside the probe (e.g., fluid) in the optical path and less chance of the beam being clipped as it exits the probe. As shown in FIG. 12, the angle-polished reflective distal end of the fiber is near the outside perimeter of the probe which increases the resolution (e.g., as a result of minimizing beam broadening) and increases the depth into the sample that the beam of electromagnetic energy can penetrate into the tissue.

Figure 13A:
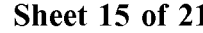
FIGS. 13A and 13B shows examples of B-mode images generated using an imaging probe such as that shown in FIG. 12 in which the end of the fiber is polished at an angle of 45°.
Figure 13B:
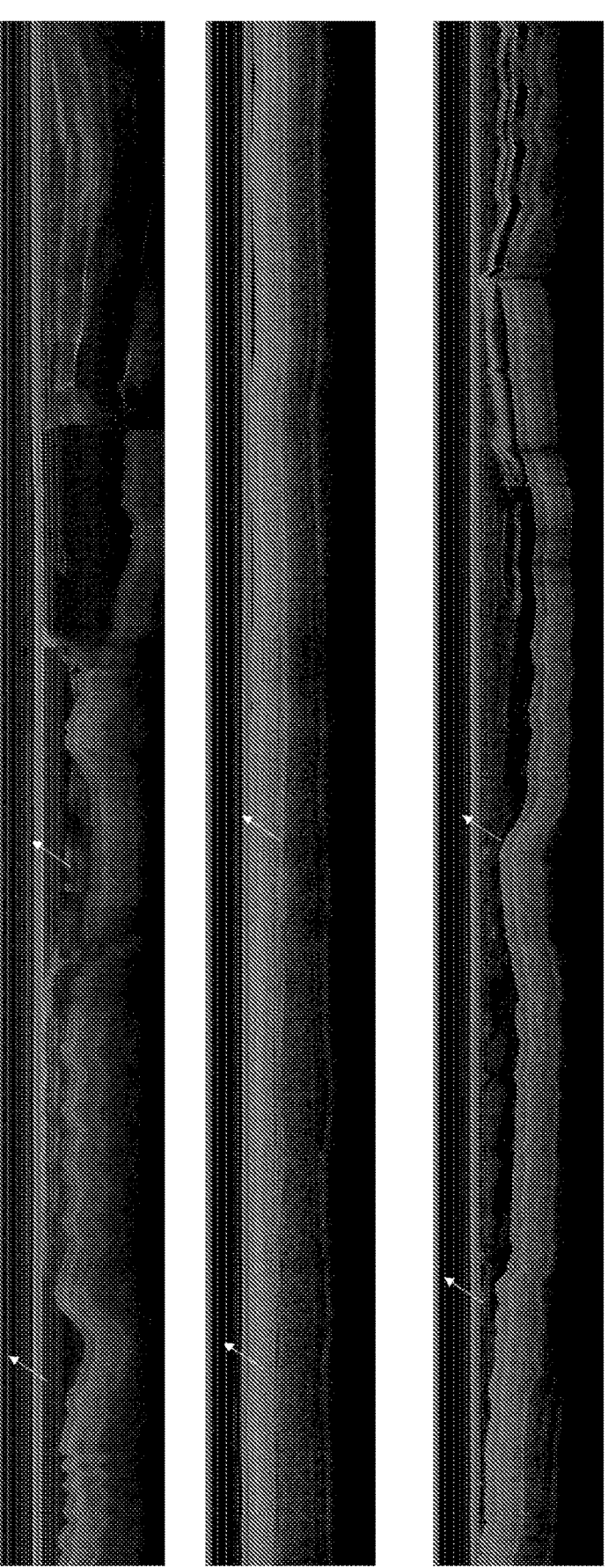

As seen in FIG. 12, the end of the optical fiber may be polished at an angle to create a reflective surface in order to direct electromagnetic radiation to the side onto the sample and to direct reflected radiation from the sample back into the fiber. When the polished angle is 45°, light is directed out of the probe at an angle of 90°, i.e., normal to the surface of the probe. Under these conditions, it has been noted that optical artifacts may be observed in the final B-mode images that are formed (see FIGS. 13A, 13B). FIGS. 13A and 13B show the presence of artifacts in the form of horizontal lines outside of the sheath (indicated by arrows) which are due to reflections (e.g., Fresnel reflections) from the sheath encasing the optical probe.

Figure 14:
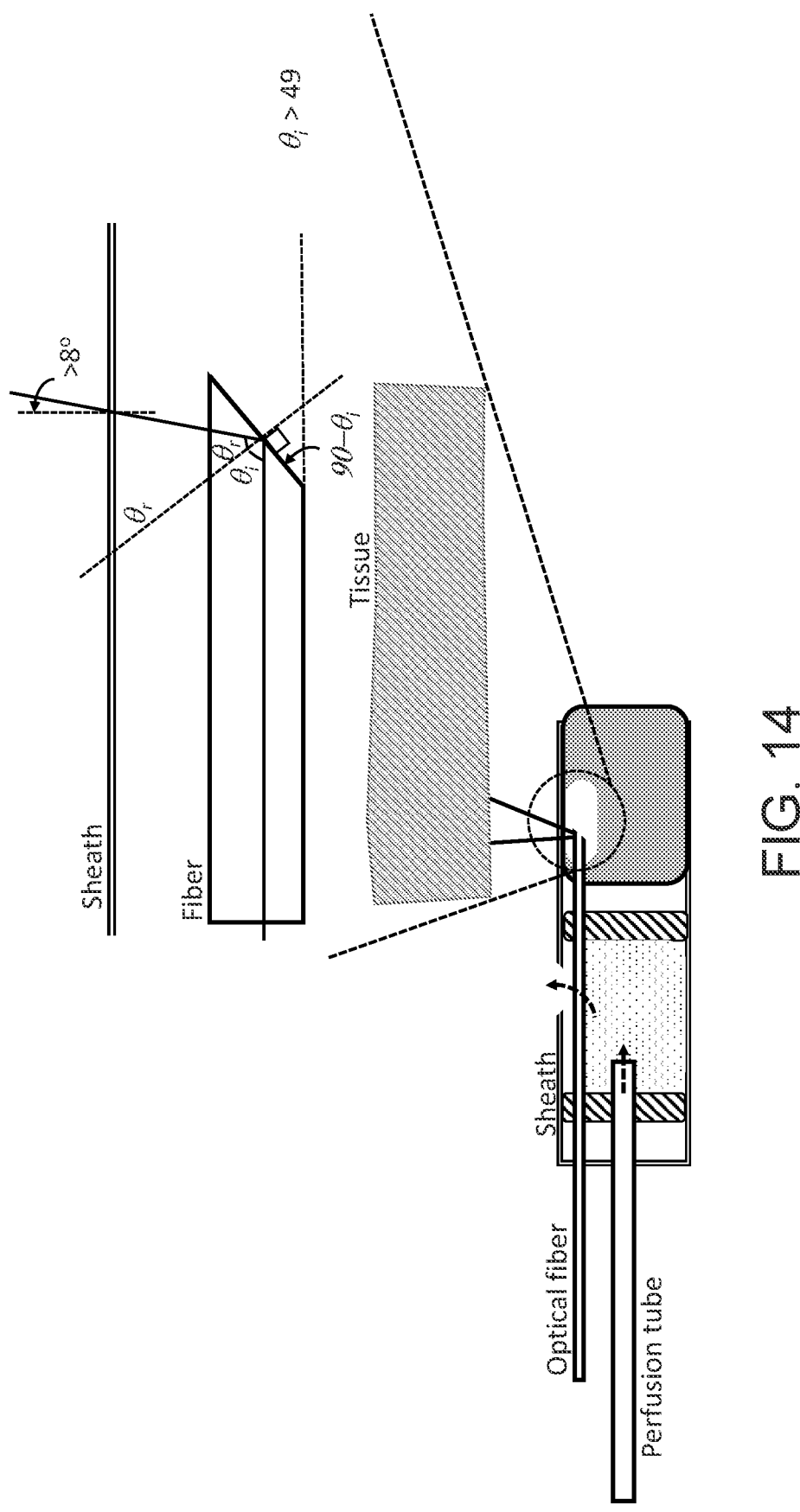
FIG. 14 shows an imaging probe according to some embodiments in which the angle at which the end of the fiber is polished is optimized in order to reduce or eliminate reflection artifacts.
Figure 15A:
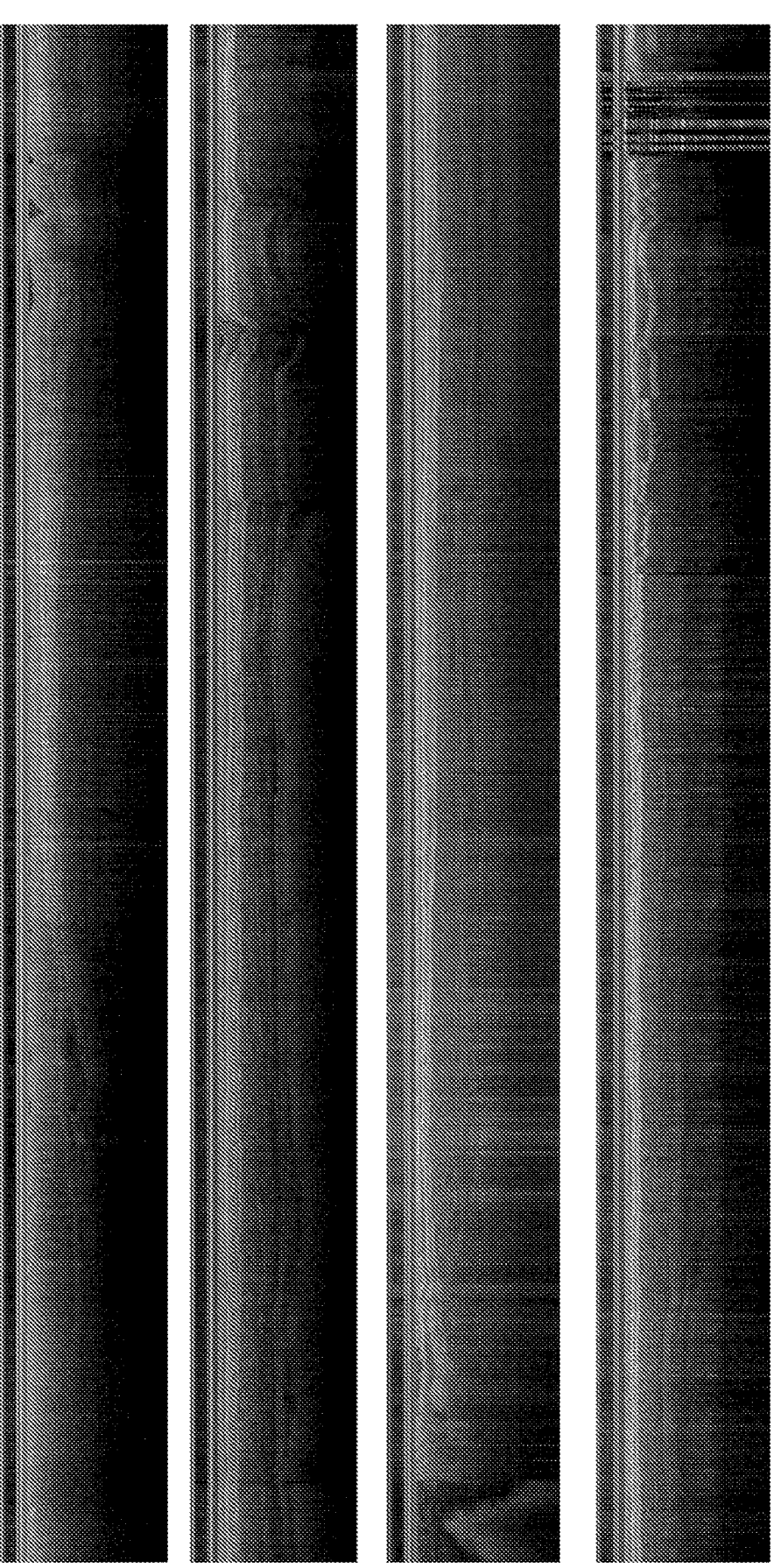
FIGS. 15A and 15B show examples of B-mode images generated using an imaging probe such as that shown in FIG. 14 in which the end of the fiber is polished at an angle of 50°.
Figure 15B:
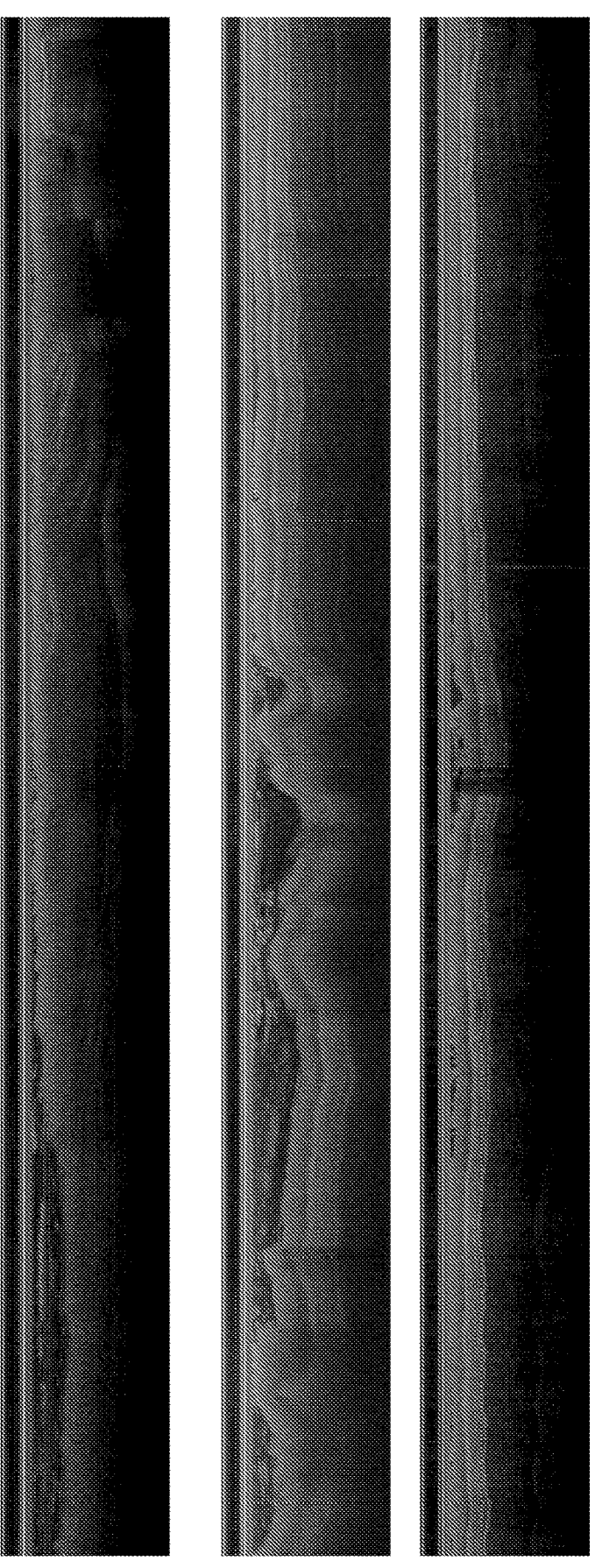

Thus, it has been determined that adjusting the angle at which the end of the fiber is polished may help avoid these artifacts. As shown in FIG. 14, these artifacts may be reduced or eliminated as the polishing angle diverges from 45° and the angle of incidence of the electromagnetic radiation traveling to and from the probe diverges from 90°. For example, as shown in FIG. 14 the polishing angle should be $(90-\theta_i)$, where $\theta_i$ is >49°, such that the fiber should be polished at an angle of 41° or less relative to the long axis of the probe. FIGS. 15A and 15B show examples of reconstructed B-mode images that were collected using a probe in which the fiber was polished at an angle of 41° relative to the long axis of the fiber and which show that the artifacts that were present when the polishing angle was 45° (see FIGS. 13A, 13B) are no longer present.

In some embodiments the optical probe may include a perfusion system for perfusing the tissue that is being imaged (see FIGS. 12 and 14). As shown in FIGS. 12 and 14, a perfusion tube may connect to a chamber within the probe which includes an opening on the side of the probe on which imaging is performed.

Figure 16:
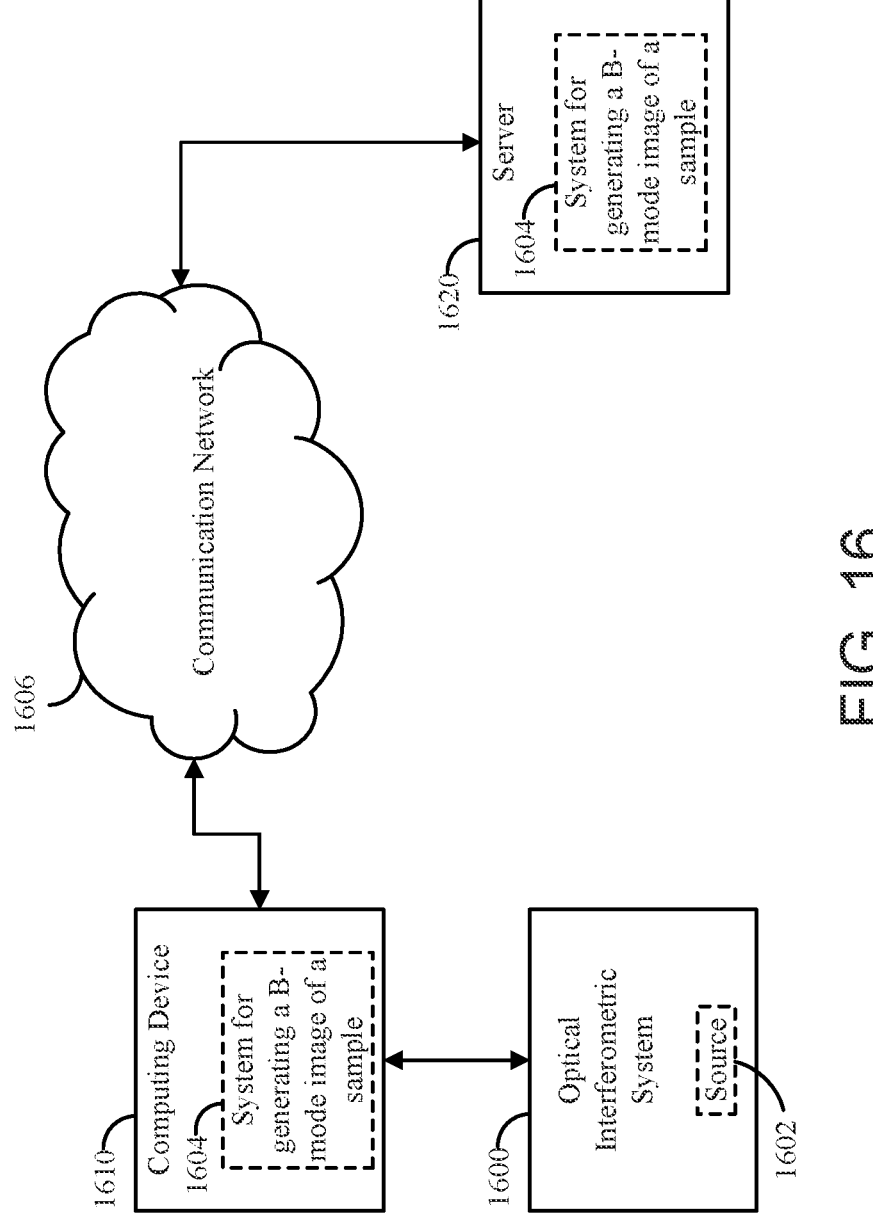
FIG. 16 shows an example of a system for generating a B-mode image of a sample in accordance with some embodiments of the disclosed subject matter.

Turning to FIG. 16, an example 1600 of a system (e.g., a data collection and processing system) for generating a B-mode image of a sample is shown in accordance with some embodiments of the disclosed subject matter. As shown in FIG. 16, a computing device 1610 can receive interferometric data from an optical interferometric system 1600. In some embodiments, computing device 1610 can execute at least a portion of a system for generating a B-mode image of a sample 1604 based on the interferometric data received from optical interferometric system 1600. Additionally or alternatively, in some embodiments, computing device 1610 can communicate information about the interferometric data received from optical interferometric system 1600 to a server 1620 over a communication network 1606, which can execute at least a portion of system for generating a B-mode image of a sample 1604 based on the interferometric data. In some such embodiments, server 1620 can return information to computing device 1610 (and/or any other suitable computing device) indicative of an output of system for generating a B-mode image of a sample 1604. This information may be transmitted and/or presented to a user (e.g., a researcher, an operator, a clinician, etc.) and/or may be stored (e.g., as part of a research database or a medical record associated with a subject).

In some embodiments, computing device 1610 and/or server 1620 can be any suitable computing device or combination of devices, such as a desktop computer, a laptop computer, a smartphone, a tablet computer, a wearable computer, a server computer, a virtual machine being executed by a physical computing device, etc. As described herein, system for generating a B-mode image of a sample 1604 can present information about the interferometric data, and/or the generated B-mode image to a user (e.g., researcher and/or physician).

In some embodiments, optical interferometric system 1600 may include an electro-magnetic radiation source 1602, which can be any source suitable for optical interferometry such as OCT. In other embodiments, electro-magnetic radiation source 1602 can be local to computing device 1610. For example, electro-magnetic radiation source 1602 may be incorporated with computing device 1610 (e.g., computing device 1610 can be configured as part of a device for capturing and/or storing optical interferometric information). As another example, electro-magnetic radiation source 1602 may be connected to computing device 1610 by a cable, a direct wireless link, etc. Additionally or alternatively, in some embodiments, electro-magnetic radiation source 1602 can be located locally and/or remotely from computing device 1610, and can communicate information to computing device 1610 (and/or server 1620) via a communication network (e.g., communication network 1606).

In some embodiments, communication network 1606 can be any suitable communication network or combination of communication networks. For example, communication network 1606 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 1606 can be a local area network, a wide area network, a public network (e.g., the Internet), a private or semi-private network (e.g., a corporate or university intranet), any other suitable type of network, or any suitable combination of networks. Communications links shown in FIG. 16 can each be any suitable communications link or combination of communications links, such as wired links, fiber optic links, Wi-Fi links, Bluetooth links, cellular links, etc.

Figure 17:
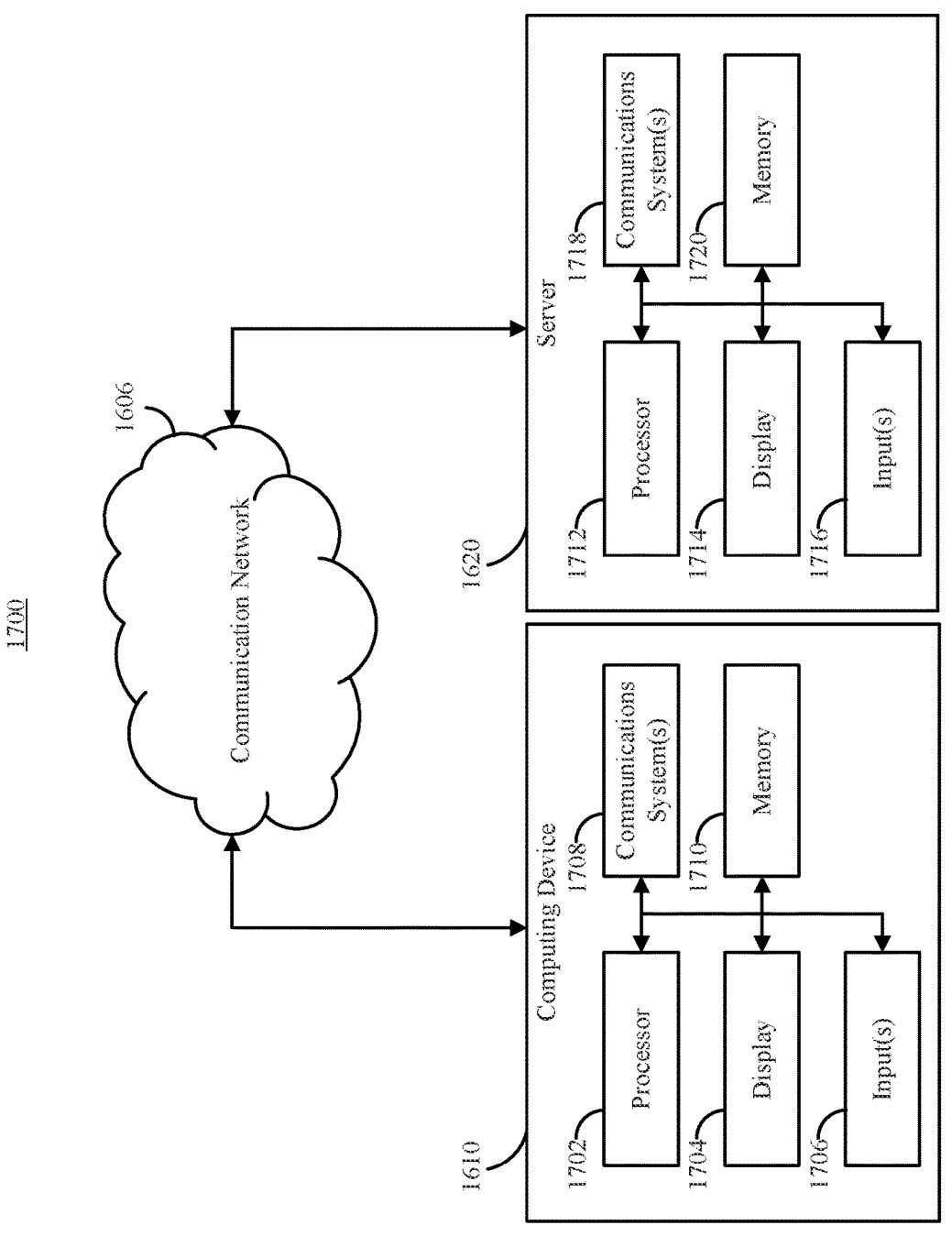
FIG. 17 shows an example of hardware that can be used to implement a computing device and server in accordance with some embodiments of the disclosed subject matter.

FIG. 17 shows an example 1700 of hardware that can be used to implement computing device 1610 and server 1620 in accordance with some embodiments of the disclosed subject matter. As shown in FIG. 17, in some embodiments, computing device 1610 can include a processor 1702, a display 1704, one or more inputs 1706, one or more communication systems 1708, and/or memory 1710. In some embodiments, processor 1702 can be any suitable hardware processor or combination of processors, such as a central processing unit, a graphics processing unit, etc. In some embodiments, display 1704 can include any suitable display devices, such as a computer monitor, a touchscreen, a television, etc. In some embodiments, inputs 1706 can include any suitable input devices and/or sensors that can be used to receive user input, such as a keyboard, a mouse, a touchscreen, a microphone, etc.

In some embodiments, communications systems 1708 can include any suitable hardware, firmware, and/or software for communicating information over communication network 1606 and/or any other suitable communication networks. For example, communications systems 1708 can include one or more transceivers, one or more communication chips and/or chip sets, etc. In a more particular example, communications systems 1708 can include hardware, firmware, and/or software that can be used to establish a Wi-Fi connection, a Bluetooth connection, a cellular connection, an Ethernet connection, etc.

In some embodiments, memory 1710 can include any suitable storage device or devices that can be used to store instructions, values, etc., that can be used, for example, by processor 1702 to present content using display 1704, to communicate with server 1620 via communications system(s) 1708, etc. Memory 1710 can include any suitable volatile memory, non-volatile memory, storage, or any suitable combination thereof. For example, memory 1710 can include RAM, ROM, EEPROM, one or more flash drives, one or more hard disks, one or more solid state drives, one or more optical drives, etc. In some embodiments, memory 1710 can have encoded thereon a computer program for controlling operation of computing device 1610. In such embodiments, processor 1702 can execute at least a portion of the computer program to present content (e.g., images, user interfaces, graphics, tables, etc.), receive content from server 1620, transmit information to server 1620, etc.

In some embodiments, server 1620 can include a processor 1712, a display 1714, one or more inputs 1716, one or more communications systems 1718, and/or memory 1720. In some embodiments, processor 1712 can be any suitable hardware processor or combination of processors, such as a central processing unit, a graphics processing unit, etc. In some embodiments, display 1714 can include any suitable display devices, such as a computer monitor, a touchscreen, a television, etc. In some embodiments, inputs 1716 can include any suitable input devices and/or sensors that can be used to receive user input, such as a keyboard, a mouse, a touchscreen, a microphone, etc.

In some embodiments, communications systems 1718 can include any suitable hardware, firmware, and/or software for communicating information over communication network 1606 and/or any other suitable communication networks. For example, communications systems 1718 can include one or more transceivers, one or more communication chips and/or chip sets, etc. In a more particular example, communications systems 1718 can include hardware, firmware and/or software that can be used to establish a Wi-Fi connection, a Bluetooth connection, a cellular connection, an Ethernet connection, etc.

In some embodiments, memory 1720 can include any suitable storage device or devices that can be used to store instructions, values, etc., that can be used, for example, by processor 1712 to present content using display 1714, to communicate with one or more computing devices 1610, etc. Memory 1720 can include any suitable volatile memory, non-volatile memory, storage, or any suitable combination thereof. For example, memory 1720 can include RAM, ROM, EEPROM, one or more flash drives, one or more hard disks, one or more solid state drives, one or more optical drives, etc. In some embodiments, memory 1720 can have encoded thereon a server program for controlling operation of server 1620. In such embodiments, processor 1712 can execute at least a portion of the server program to transmit information and/or content (e.g., results of a tissue identification and/or classification, a user interface, etc.) to one or more computing devices 1610, receive information and/or content from one or more computing devices 1610, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

In some embodiments, the optical signals are detected by photodiodes. It should be recognized that any opto-electronic conversion device including but not limited to photo detectors, photodiodes, line-scan and two-dimensional cameras, and photodiode arrays can be used to perform this detection function.

It should be noted that, as used herein, the term mechanism can encompass hardware, software, firmware, or any suitable combination thereof.

It should be understood that the above described steps of the herein-described processes can be executed or performed in any order or sequence not limited to the order and sequence shown and described in the figures. Also, some of the steps of the herein-described can be executed or performed substantially simultaneously where appropriate or in parallel to reduce latency and processing times.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A method for generating a B-mode image of a sample, comprising:

obtaining a plurality of M-mode frames from the sample using a probe;

combining the plurality of M-mode frames into a montage, the montage comprising a plurality of A-lines corresponding to the respective plurality of M-mode frames;

comparing adjacent A-lines of the montage to identify at least one pair of correlated A-lines; and removing one of the at least one pair of correlated A-lines from the montage to generate a B-mode image.

2. The method of claim 1, wherein obtaining the plurality of M-mode frames using a probe further comprises:

capturing the plurality of M-mode frames using an optical coherence tomography (OCT) probe.

3. The method of claim 2, wherein capturing the plurality of M-mode frames using an OCT probe further comprises:

capturing the plurality of M-mode frames while not rotating the OCT probe.

4. The method of claim 3, wherein capturing the plurality of M-mode frames using an OCT probe further comprises:

capturing the plurality of M-mode frames using an OCT probe based on manually translating the OCT probe in a direction parallel to a long axis of the sample.

5. The method of claim 1, wherein removing one of the at least one pair of correlated A-lines from the montage to generate a B-mode image further comprises:

generating the B-mode image based on processing the montage such that no adjacent A-lines are correlated with one another.

6. The method of claim 1, wherein comparing adjacent A-lines of the montage further comprises:

comparing adjacent A-lines of the montage based on computing a correlation coefficient, and comparing the computed correlation coefficient to a threshold value to identify the at least one pair of correlated A-lines.

7. The method of claim 6, wherein comparing adjacent A-lines of the montage to identify at least one pair of correlated A-lines further comprises:

evaluating a speckle pattern of the generated B-mode image to determine a speckle pattern length, comparing the speckle pattern length to a speckle pattern threshold, and adjusting the threshold value based on comparing the speckle pattern length to the speckle pattern threshold.

8. The method of claim 1, further comprising at least one of storing, transmitting, or displaying the generated B-mode image.

9. The method of claim 1, further comprising improving a signal-to-noise level of the generated B-mode image by averaging pairs of adjacent A-lines of the generated B-mode image.

10. The method of claim 1, further comprising:

identifying a presence of an artifact in the generated B-mode image, determining a maximum scanning rate, and wherein obtaining a plurality of M-mode frames from the sample further comprises:

obtaining a plurality of M-mode frames from the sample at a scan rate that is less than or equal to the maximum scanning rate.

11. The method of claim 1, wherein, after obtaining a plurality of M-mode frames from the sample using a probe, the method further comprises:

compensating for a curvature in each of the plurality of M-mode frames based aligning a plurality of bright spots corresponding to a reflection from the probe such that the plurality of bright spots are in a straight line.

12. A system for generating a B-mode image of a sample, comprising:

an optical probe coupled to an electromagnetic radiation source and a detector; and a processor coupled to the electromagnetic radiation source and the detector and configured to:

obtain a plurality of M-mode frames from the sample;

combine the plurality of M-mode frames into a montage, the montage comprising a plurality of A-lines corresponding to the respective plurality of M-mode frames;

compare adjacent A-lines of the montage to identify at least one pair of correlated A-lines; and remove one of the at least one pair of correlated A-lines from the montage to generate a B-mode image.

13. The system of claim 12, wherein the processor, when obtaining the plurality of M-mode frames, is further configured to:

capture the plurality of M-mode frames using optical coherence tomography (OCT).

14. The system of claim 13, wherein the optical probe comprises an OCT probe, and wherein the processor, when capturing the plurality of M-mode frames, is further configured to:

capture the plurality of M-mode frames using the OCT probe, wherein the OCT probe is not rotated.

15. The system of claim 14, wherein the processor, when capturing the plurality of M-mode frames using the OCT probe, is further configured to:

capture the plurality of M-mode frames using the OCT probe based on manually translating the OCT probe in a direction parallel to a long axis of the sample.

16. The system of claim 12, wherein the processor, when removing one of the at least one pair of correlated A-lines from the montage to generate a B-mode image, is further configured to:

generate the B-mode image based on processing the montage such that no adjacent A-lines are correlated with one another.

17. The system of claim 12, wherein the processor, when comparing adjacent A-lines frames of the montage, is further configured to:

compare adjacent A-lines of the montage based on computing a correlation coefficient, and compare the computed correlation coefficient to a threshold value to identify the at least one pair of correlated A-lines.

18. The system of claim 17, wherein the processor, when comparing adjacent A-lines of the montage to identify at least one pair of correlated A-lines, is further configured to:

evaluate a speckle pattern of the generated B-mode image determine a speckle pattern length, compare the speckle pattern length to a speckle pattern threshold, and adjust the threshold value based on comparing the speckle pattern length to the speckle pattern threshold.

19. The system of claim 12, wherein the processor is further configured to at least one of store, transmit, or display the generated B-mode image.

20. The system of claim 12, wherein the processor is further configured to improve a signal-to-noise level of the generated B-mode image based on averaging pairs of adjacent A-lines of the generated B-mode image.

21. The system of claim 12, wherein the processor is further configured to:

identify a presence of an artifact in the generated B-mode image, determine a maximum scanning rate, and wherein the processor, when obtaining a plurality of M-mode frames from the sample, is further configured to:

obtain a plurality of M-mode frames from the sample at a scan rate that is less than or equal to the maximum scanning rate.

22. The system of claim 12, wherein the optical probe comprises an optical fiber.

23. The system of claim 22, wherein the distal end of the optical fiber is polished at an angle of 41° or less relative to a long axis of the probe.

24. The system of claim 22, wherein the optical fiber is disposed away from a central axis of the probe.

25. The system of claim 24, wherein the optical fiber is adjacent to a side of the probe from which electromagnetic radiation is emitted.

* * * * *